(12) United States Patent
Truex et al.

(10) Patent No.: US 7,425,310 B2
(45) Date of Patent: Sep. 16, 2008

(54) APPARATUS, SYSTEM, AND METHOD OF DETECTING AN ANALYTE UTILIZING PYROELECTRIC TECHNOLOGY

(76) Inventors: Bryan Truex, 521 Belle Isle Ave., Belleair Beach, FL (US) 33786; Charles Loomis, 18104 Diamond Cove Ct., Tampa, FL (US) 33647

( * ) Notice: Subject to any disclaimer, the term of this patent is extended or adjusted under 35 U.S.C. 154(b) by 253 days.

(21) Appl. No.: 11/045,693

(22) Filed: Jan. 29, 2005

(65) Prior Publication Data

US 2005/0196322 A1    Sep. 8, 2005

Related U.S. Application Data

(60) Provisional application No. 60/540,308, filed on Jan. 29, 2004.

(51) Int. Cl.
*G01N 21/00* (2006.01)
*G01N 25/20* (2006.01)
*G01N 27/00* (2006.01)
*G01N 33/00* (2006.01)
*G01N 33/53* (2006.01)

(52) U.S. Cl. ............... 422/82.05; 422/68.1; 422/82.01; 435/7.1; 435/7.93; 435/7.94; 436/147

(58) Field of Classification Search ............... 436/147
See application file for complete search history.

(56) References Cited

U.S. PATENT DOCUMENTS

| | | | | |
|---|---|---|---|---|
| 4,076,420 A | * | 2/1978 | De Maeyer et al. ........... 356/73 |
| 4,661,320 A | * | 4/1987 | Ito et al. ..................... 422/86 |
| 4,895,809 A | * | 1/1990 | Schlabach et al. ........... 436/518 |
| 4,941,742 A | * | 7/1990 | Schrader et al. ............. 356/38 |
| 5,464,588 A | * | 11/1995 | Bather et al. ................ 422/88 |
| 5,585,275 A | * | 12/1996 | Hudson et al. .............. 436/518 |
| 5,622,868 A | * | 4/1997 | Clarke et al. ................ 436/147 |
| 5,736,188 A | * | 4/1998 | Alcock et al. ............... 427/2.11 |
| 5,910,854 A | * | 6/1999 | Varaprasad et al. ......... 359/273 |

(Continued)

OTHER PUBLICATIONS

Capineri et al., "Comparisons between PZT and PVDF thick films technologies in the design of low-cost pyroelectric sensors", 2004, Review of Scientific Instruments, vol. 73, pp. 4906-4910.*

(Continued)

*Primary Examiner*—Long V. Le
*Assistant Examiner*—Unsu Jung
(74) *Attorney, Agent, or Firm*—Goldizen & Associates; Bradley D. Goldizen

(57) ABSTRACT

A system for the measurement of a target analyte is provided including a detection apparatus and a reading apparatus. The detection apparatus, or "carrier", includes a pyroelectric transducer ("pyroelectric film") and one or more reagent concentrations ("reagent deposit") deposited on the film. The reagent deposits are adapted to react with, and thus, detect the presence of a target analyte present in the local environment. Upon detection of the target analyte by the reagent deposit, the reading apparatus and the pyroelectric film may be used to detect the amount of heat that can be absorbed by the reagent deposit in response to irradiation. The pyroelectric film then delivers to the reader a signal corresponding to heat detected and the reader provides a corresponding indication of the concentration of the target substance detected.

61 Claims, 21 Drawing Sheets

U.S. PATENT DOCUMENTS

| | | | | |
|---|---|---|---|---|
| 5,923,421 | A * | 7/1999 | Rajic et al. | 356/328 |
| 5,965,456 | A * | 10/1999 | Malmqvist et al. | 436/514 |
| 6,087,184 | A * | 7/2000 | Magginetti et al. | 436/514 |
| 6,106,149 | A * | 8/2000 | Smith | 374/31 |
| 6,326,215 | B1 * | 12/2001 | Keen | 436/518 |
| 6,443,616 | B1 * | 9/2002 | Brotz | 374/17 |
| 6,743,581 | B1 * | 6/2004 | Vo-Dinh | 435/6 |
| 6,886,421 | B2 * | 5/2005 | Mathur et al. | 73/864.81 |
| 2002/0150503 | A1 * | 10/2002 | Tanaka et al. | 422/58 |
| 2004/0141879 | A1 * | 7/2004 | Loomis et al. | 422/58 |
| 2005/0014282 | A1 * | 1/2005 | Schrof et al. | 436/164 |
| 2005/0079627 | A1 * | 4/2005 | Jones et al. | 436/164 |

OTHER PUBLICATIONS

Colin et al., "Development of a piezo-optical chemical monitoring system for nitrogen dioxide", 1998, Sensors & Actuators B, vol. 51, pp. 244-248.*

Gibson et al., "Kinetic factors in the response of piezo-optical chemical monitoring devices", 1998, Sensors & Actuators B, vol. 51, pp. 238-243.*

Sahraoui et al., "The application of the photopyroelectric method for measuring the thermal parameters of pyroelectric materials", 2002, Review of Scientific Instruments, vol. 73, pp. 2766-2772.*

Keiji et al., "Pyroelectric photothermal spectroscopy for thin solid films", 1988, J. Appl. Phys., vol. 63, pp. 1815-1819.*

Wright et al., "Development of a piezo-optical chemical monitoring system", 1998, Sensors & Actuators B, vol. 51, pp. 121-130.*

"Process Steps in Product-by-Process Claims are Held Not to be Claim Limitations", Association of Patent Law Firms, Issue 06/16, Mar. 14, 2006.*

* cited by examiner

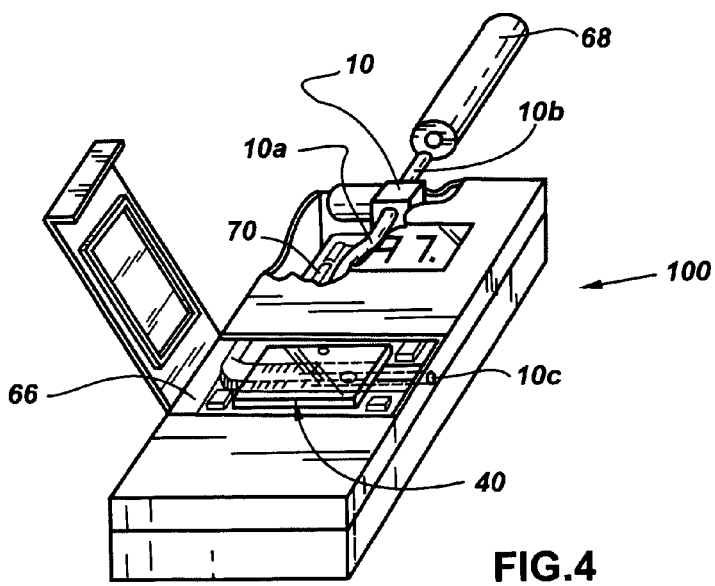
FIG.4
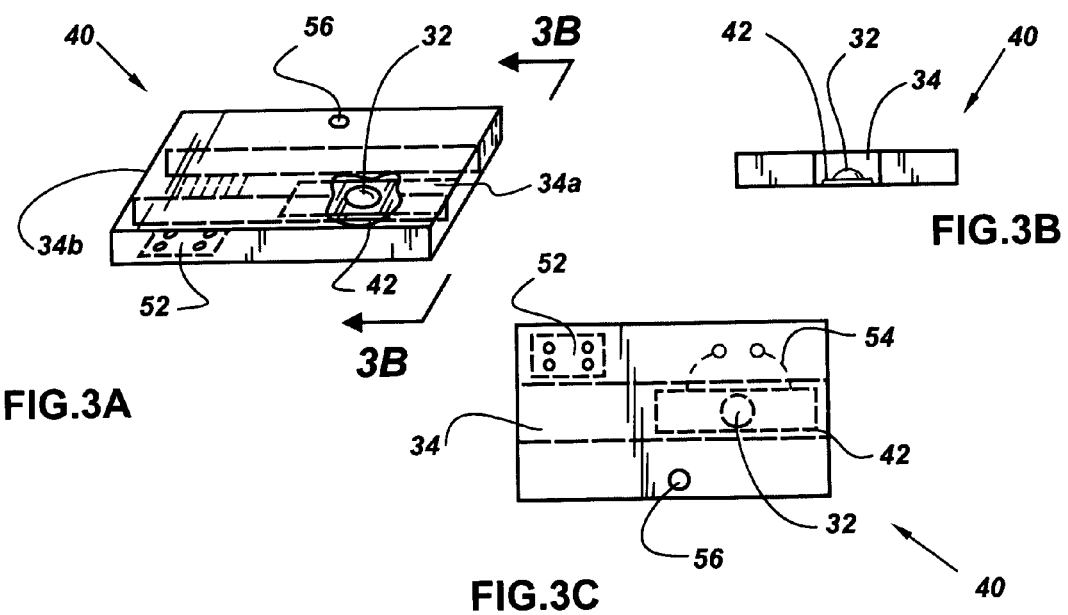
FIG.3A
FIG.3B
FIG.3C

APPARATUS, SYSTEM, AND METHOD OF DETECTING AN ANALYTE UTILIZING PYROELECTRIC TECHNOLOGY

This application claims priority from U.S. Provisional Patent Application Ser. No. 60/540,308 filed on Jan. 29, 2004.

The patent application did not receive federal research and development funds.

BACKGROUND OF THE INVENTION

The present invention relates generally to an apparatus, system, and method of detecting a target substance, i.e., an analyte, such as a gas, in a local environment. More particularly, the invention is such a system, apparatus, and method that employs or incorporates pyroelectric or piezoelectric technology.

It is often desirable, advantageous, or simply necessary to monitor the environment around a work place, home or other sites. For example, in many industrial environments, hazards may exist in the form of toxic, carcinogen, flammable, corrosive chemicals and harmful, radiochemical and biological materials. This is especially a concern when the harmful chemicals or substances are not readily detectable, e.g., odorless or invisible to the human senses. These environments may be constantly monitored by safety personnel equipped with portable testing equipment, including gas detectors, other instruments, water kits, radiation detectors, other instruments for detecting biological materials and other harmful chemicals and contaminants. Alternatively, personnel may be required to wear or carry field detection devices, such as badges, that provide an observable alarm when certain levels of the harmful chemicals are detected. In addition, monitoring equipment may be permanently placed at strategic locations to alert personnel of dangerous conditions, or the presence of pollutants and contaminants.

The present invention is related to systems, apparatus and methods described in U.S. Provisional Application No. 60/306,469, filed Jul. 18, 2001, International Application PCT/US02/23309 filed Jul. 18, 2002, and U.S. patent application Ser. No. 10/475,157, filed Oct. 15, 2003. Each of these applications is hereby incorporated by reference and made a part of the present disclosure for background purposes. The above-described applications are just some of the applications in which the present invention and its various aspects may be suited for use. It should be understood, however, that terms used to describe the present invention and certain embodiments and aspects of the present invention are adequately defined and explained herein and may possibly deviate or expand, by Applicants' choice, from earlier definitions and explanations for purposes relevant to only to the present description (and thus, should not impact any reading and/or interpretation of these earlier filed applications).

SUMMARY OF THE INVENTION

In one aspect of the present invention, a system for the measurement of a target analyte is provided. The system includes a detection apparatus and a reading apparatus. The detection apparatus, or "carrier", includes a pyroelectric or piezoelectric transducer (hereinafter "pyroelectric film") and one or more reagent concentrations ("reagent deposits") deposited on (or on a separate substrate in the vicinity of) the film and adapted to react with, and thus, detect the presence of a target analyte in the local environment. The reagent deposit is further adapted to exposure to an electromagnetic emitting source. The pyroelectric film detects the light absorption of the reagent deposit as microscopic heating. This microscopic heating produces an output that is processed to derive the measurement of the target substance. In this manner, the pyroelectric film is used to indicate the amount of or concentration of the target analyte in the environment. U.S. Pat. No. 5,622,868 describes technology that is related to and at least partly applicable to the invention, and thus, hereby incorporated by reference for all purposes and made part of the present disclosure.

A reading apparatus is provided that is operable with a detection apparatus described above. Such a reading apparatus includes an electromagnetic emitting source (e.g., light emitting diode (LED)) that is operable with the pyroelectric film and a reagent deposit to indicate the amount or concentration of the target analyte. The reading apparatus and the detection apparatus may be two distinct devices or may be incorporated into a single device. The electromagnetic source may be optionally mounted on a removable, modular subassembly such that it can be interchanged to provide the optimum energy source for the application.

As used herein, the term "indication" or "indicating" shall mean measuring, monitoring, or otherwise communicating the detection of the target substance to the user in a quantitative and/or qualitative manner, including the measurement and display of the amount or concentration of the target substance in the local environment or the detection of a specified amount or concentration of the target substance. Such communication may be performed visually, audibly, or by tactile sense. Also, as used herein, a "reagent deposit" shall mean a concentration of reagent applied to a surface and shall not be limited to any specific shape, form, quantity, concentration or substance.

One system according to the invention will include a carrier having one or more reagent deposits deposited thereon. In one embodiment, the reagent deposits are arranged in predetermined sets, with the sets provided in containers. The system further includes pyroelectric film positioned adjacent the reagent deposits, and a reader operatively associated with the pyroelectric film (e.g., including a light emitting source for illuminating the reagent deposit). Note that a set of reagent deposits may consist of one reagent deposit. The system may also include a pump (or some other means of moving fluids and/or solids such as a fan, pressure or vacuum generating device, etc.) for moving a sample of the local environment past or in the vicinity of the container containing the set, so as to initiate a reaction between the reagent deposit and the target analyte to provide detection and indication of the target analyte. Among other elements, the preferred system may also include a filter operable with the pump and/or one or more alarms for indicating the presence of the target analyte. The filter may be optionally mounted on a removable, modular subassembly such that it can be interchanged to provide the optimum filter for the application.

The present invention is further directed to a method of employing the system and/or the system described above. Such an inventive method allows for the detection and indication of one or more target analytes such as a target gas. In another embodiment, the method allows for the indication of the amount or concentration of the target analyte in real-time. Thus, in one aspect of the invention, the method provides for the substantially simultaneous detection and indication of an amount of the target analyte in the local environment.

In a system for measuring or otherwise indicating the concentration of at least one target analyte, a sensor carrier subsystem, according to the invention, includes a transparent substrate having a first surface, a second surface disposed opposite of the first surface, and a reagent deposit. The reagent deposit (e.g., a colorimetrically reactive reagent, fluorescent and luminescent clot) is supported on the first surface and is reactive when exposed to the target analyte. The reagent deposit is further characterized by a capacity to absorb electromagnetic energy (e.g., visible light, IR, near IR, UV light and microwave), wherein the absorption capacity changes after the reagent deposit reacts upon exposure to the target analyte. An electromagnetic spectrum emitting source or EM source (e.g. light emitting diode) is positioned proximal to the transparent substrate and closer to the second surface than to the first surface. The EM source is operable to irradiate the reagent deposit by way of a path directed through the transparent substrate. A pyroelectric transducer is positioned proximal to the reagent deposit to detect energy absorbed by the reagent deposit upon irradiation by the EM source and to generate output signals indicative of the detected energy, such that the output signal is indicative of exposure to the target analyte. Thus the energy absorbed by the reagent deposit varies when the reagent deposit is exposed to the target analyte. By recognizing this change in absorbed energy, a system can be realized that indicates the presence of the target analyte.

Several variations of the carrier subsystem are possible and are within the scope of the invention. In one embodiment, the pyroelectric transducer is positioned intermediate the transparent substrate and the EM source, such that the EM source is operable to irradiate the reagent deposit by way of a path directed through the pyroelectric transducer and through the transparent substrate. Alternatively, the transparent substrate is positioned intermediate the transducer and the EM source. In another variation, the carrier subsystem includes a second EM source positioned proximal the reagent deposit such that the first surface is positioned intermediate the second surface and the second EM source. In a further variation, the pyroelectric transducer (preferably transparent) is positioned intermediate the transparent substrate and the second EM source, such that the second EM source is operable to irradiate the reagent deposit by way of a path directed through the pyroelectric transducer.

In yet another variation, the reagent deposit is supported on the transparent substrate such that the reagent deposit faces and is spaced apart from the pyroelectric transducer. The transparent substrate and the pyroelectric transducer are spaced apart so as to provide a sample environment flow path therebetween. In another variation, the transparent substrate further includes a second reagent deposit supported on the second surface. The second reagent deposit may be disposed on the second surface in generally vertical alignment with the first reagent deposit supported on the first surface. Moreover, a second EM source may be positioned relative to the first EM source, such that the transparent substrate, the first and second reagent deposits, and the pyroelectric transducer are positioned intermediate the first and second EM sources. Alternatively, a second EM source may be positioned proximal the first EM source, such that the pyroelectric transducer is positioned intermediate the transparent substrate and the first and second EM sources.

In yet another variation, the carrier subsystem includes a second substrate supporting a reagent deposit on a first surface and spaced apart from the pyroelectric transducer such that the second reagent deposit faces the pyroelectric transducer. The EM source is operable to irradiate the second reagent deposit by way of a path directed through the transparent substrate and through the pyroelectric transducer. Alternatively, the second transparent substrate has a first surface and a second surface disposed opposite of the first surface, and a second reagent deposit is supported on the first surface and spaced apart from the pyroelectric transducer. The second reagent deposit faces the pyroelectric transducer. Further, a second EM source is positioned proximal the second surface of the second transparent substrate and is operable to irradiate the second reagent deposit by way of a path directed through the first and second surfaces of the second transparent substrate.

In another aspect of the invention, the carrier subsystem includes a reflective surface positioned to redirect energy emitted by the EM source to the reagent deposit. The reflective surface is positioned relative to the EM source such that the transparent substrate, the reagent deposit, and the pyroelectric transducer are positioned intermediate the reflective surface and the EM source. Preferably, the reflective surface comprises a mirror, a wave-guide or the like.

The invention is also directed to a method of detecting the presence of a target analyte in a sample environment utilizing a reagent deposit reactive to exposure to the target analyte and further characterized by a capacity to absorb electromagnetic energy irradiated thereupon, wherein the absorption capacity changes after a reaction to exposure. The inventive method comprises several steps. In an initial step, a transparent substrate is provided having a first surface, a second surface disposed opposite the first surface, and a reagent deposit supported on the first surface. An electromagnetic energy emitting source (EM source) is positioned relative to the transparent substrate such that the second surface is positioned intermediate the first surface and the EM source. A pyroelectric transducer for detecting energy absorbed by the reagent deposit is also positioned proximal the reagent deposit. The method further entails directing a sample environment past the proximity of the reagent deposit, thereby initiating a reaction between the reagent deposit and the target analyte. Furthermore, the EM source is operated to irradiate the reagent deposit by way of a path directed through the transparent substrate. The pyroelectric transducer is then utilized to detect the energy absorbed by the reagent deposit upon irradiation by the EM source and to generate output signals corresponding with a measure of the detected energy, such that the output signal corresponds with the degree of exposure. Thus, the amount of energy absorbed by the reagent deposit varies according to the quantity of target analyte present in the sampled environment.

BRIEF DESCRIPTION OF THE FIGURES

FIG. 3A is a simplified perspective view of a second carrier suitable for use with the system in FIG. 1.

FIG. 3B is an end view of the carrier at line 3B-3B in FIG. 3A.

FIG. 3C is a bottom view of the carrier in FIG. 3A.

FIG. 4 is a perspective view of a receiver and carrier according to the invention.

DETAILED DESCRIPTION OF THE INVENTION

Figure 1:
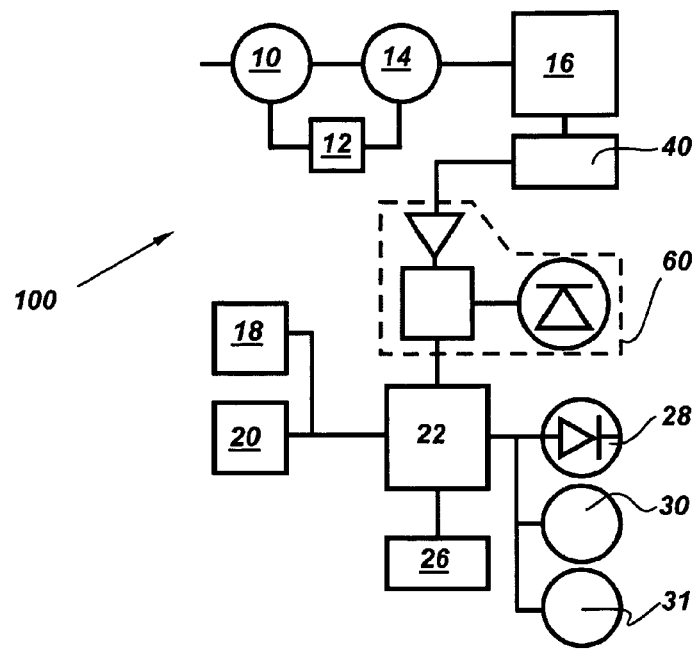
FIG. 1 is a simplified schematic representation of a gas detection and indication system and apparatus, according to the invention.

FIG. 1 is a schematic representation of a system 100 for detecting a target substance or analyte in a local gaseous, fluid or liquid environment embodying various aspects of the present invention. In the preferred embodiment, the system 100 is operable to indicate the amount or concentration of the target analyte that is detected. The invention is also directed to a method of detecting such a target analyte employing a combination of technologies and/or functions, most of which are provided by the system 100 represented by FIG. 1.

As will become apparent, the present invention is adapted for various applications. For example, the detection system 100 has applications in the general fluids detection market, particularly in the gas vapor, aerosol, and particulates detection market, as a portable or field deployable detector. In this market, one of the more frequently used portable gas detectors comes in the form of badges covered with reagents that react colorimetrically with gases in the local environment. The badges are worn by the user and can provide a visual signal, in the form of a color change, when the reagent is exposed to the target gas. At most, these badges provide only an approximate measurement of the amount of gas in the local environment, relying on the user to compare or evaluate the degree of color change. The system(s) 100 depicted in the Figures provide a preferable replacement for these badges. Target analytes contemplated by the present invention include gases, vapors, liquids, solids, aerosols, and particulates as well as biotoxins, enzymes, antibodies, DNA, proteins, spores, viruses, bacteria, other biological materials and radiation. For example, in certain applications the target analyte may be one or more of the following: merocyclic and trichothecenes; including voridon E, Satratoxins F, Satrataxins G, and Satratoxins H, Trichoverris, verrucarol and verrucarin.

Figure 2:
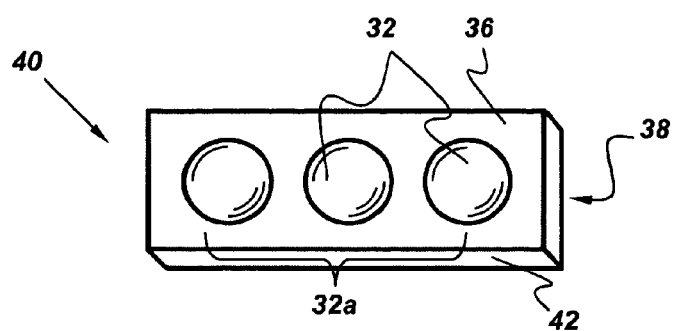
FIG. 2 is a simplified perspective view of a carrier suitable for use with the system in FIG. 1.

In one aspect of the invention, the inventive detection system 100 employs or incorporates a core detection component provided by: an optically detectable or colorimetric detection element, a pyrolectric or other thermoelectric transducer element operatively associated with the colorimeteric detection element, and one or more carriers or substrates 40 supporting or containing these two elements (see FIG. 1). Pyroelectric film (also called polyvinylidine fluoride (PVDF) or piezo film) suitable for use with the present invention is described generally in U.S. Pat. No. 5,622,868 (previously incorporated by reference above). One type of carrier 40 that is suitable for use with the inventive system is a cartridge-type carrier 40 as shown in FIGS. 2 and 3. Other types of carriers 40 also suitable for use with various embodiments of the invention are shown throughout in FIGS. 4-8. These other types and the corresponding Figures are described separately below.

Returning now to the schematic representation of FIG. 1, the detection system 100 includes a mechanism configured to receive an output from the transducer element 40 and to convert the output into a readable indication of the amount or concentration of the target substance detected. FIG. 1 illustrates one type of mechanism, a reader 60, that is suitable for use with the carrier 40 of the inventive detection system 100.

The reader 60 includes an electromagnetic irradiation or illumination source in the form of an LED to irradiate or illuminate the reagent 32. The light is pulsed with a specific frequency preferably about 50 to 60 hertz. The electrical signal produced by the heat shock or energy absorbed or emitted by the pyroelectric film in the vicinity of the reagent deposit due to colorimetric, chemical, biochemical, physical, and/or molecular changes, is interpreted by an analog to digital converter, which is then processed by a microprocessor and displayed as a reading. The illumination or irradiation source may illuminate the reagent and pyroelectric film before they are exposed to a sample environment to establish a baseline reading. This baseline reading may then be compared to a later reading after the reagent and pyroelectric film have been exposed to a sample environment to recognize a difference. The magnitude of this difference may correspond to a quantity of target analyte present in the sample environment. This microprocessor may have additional duties relating to pump control, temperature and humidity compensation of the PVDF reading, reading and writing the memory chip stored in the PVDF film cartridge (as outlined in this patent), control of alarm indicators such as visual, audible and vibration devices, and reading an optional bar code on a sensor and/or filter module. In any case, a reader suitable for use with the present invention is one that incorporates many of the basic mechanisms as described in U.S. Pat. No. 5,622,868.

FIG. 1 further illustrates the use of a pump 10 in conjunction with a flow sensor 14 and flow regulator 12 for drawing and then controlling a flow of the local gaseous environment into or across the carrier 40. A flow filter 16 may be recommended as well in certain demanding environments. As further explained below, the use of a pump 10 in the detection system 100 allows for measurements which are exceedingly more accurate and consistent than currently provided by the above-mentioned badges and other known detection systems. The pump 10 also provides face velocity at the surface of the analyte to allow a sufficient amount of analyte to expose and react with a reagent. Applicants have also found that pump 10 in this way accelerates the responsive time and sensitivity of the detection system 100. The use of a pump also allows for incorporation of filters, including high resistance filters to remove interferants and poison contaminants from the sample environment, and/or to facilitate separation and specificity of analyte that will not, otherwise, diffuse through the filter with the fluid flow.

Depending on the requirements of a particular application, the detection system 100 may include a number of sensors, alarms and other instrumentation, each of which is operable with or linked to a control mechanism 22, as shown in FIG. 1. For example, the detection system may include a digital display 26 for visually indicating the concentration of the target substance, and one or more visual alarms 28 (e.g., flashing red LED), audible alarms 30, and vibration alarm 31. The alarms may be configured to activate when certain threshold levels of the target substance are detected. The detection system 100 may also include a temperature sensor 18 and a humidity sensor 20.

In several embodiments, including the embodiment depicted in FIG. 4, a portable, self-contained housing 62 is provided to house or frame the piezofilm reader 60 and the various sensors, alarms, pump-related components, and other accessories. This housing 62 also includes a microprocessor or equivalent means for performing or controlling various functions, including conversion of pyroelectric film output to a readable digital indication. This self-contained housing 62 may be referred as to as the carrier receiving device or simply, the reader 62. In several embodiments, engagement between the carrier 40 and the reader 62 also initiates sampling of the local environment and testing for the target substance in that sample. Also, in several embodiments, the reader 62 is adapted to be field deployable, portable testing equipment.

Figure 5:
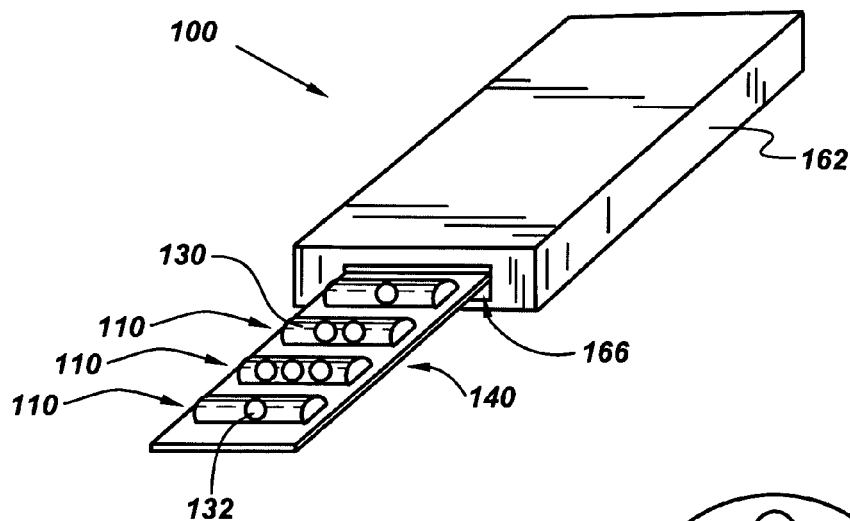
FIG. 5 is a perspective view of a second embodiment of a receiver and a carrier according to the invention.

Referring now to FIGS. 2-5, the cartridge-type carriers 40 depicted therein are separate from the reader 62 but are engageable therewith during a testing operation (and detachable therefrom for another testing operation). FIG. 4 depicts the carrier 40 in engagement with a flip-top type reader 62. FIG. 5 depicts another cartridge-type carrier being disengaged from a second type of reader 162.

The carrier 40 preferably employs a colorimetric detectable element in the form of reagents 32 that selectively react with chemicals, or target substances, in the gaseous or other fluids environment. The reagents are also characterized by the amount of electromagnetic radiation they can absorb or emit, which translates to microscopic heat shock or energy generated or absorbed within the reagent. Thus, the reagent may be irradiated with an LED or other light source or microwave or electromagnetic enery source to cause heat to be generated within the reagent. In turn, a pyroelectric film transducer is employed to measure the temperature change across the reagent, which directly corresponds to a voltage generated by the transducer. Upon exposure to the target substance, the reagent deposit undergoes a change (chemical, biochemical, physical and/or molecular), and as a result of the change, the reagent deposit's capacity to absorb or emit energy also changes. Thus, the reagent deposit may be irradiated before and after a testing operation and the corresponding change and the difference in the heat or other forms of energy generated in the reagent calculated. The calculated voltage change is then translated into a corresponding concentration of the measured analyte by the reader 62.

In the embodiment illustrated, reagents 32 preferably undergo a colorimetric change upon detection of a target analyte. As a result, the reagent's capacity to absorb light changes. Thus, the reagent deposit may be illuminated before or after a testing operation and then the difference in the heat generated due to illumination after each operation (absorption capacity) is calculated or the reagent deposit may be irradiated after the exposure to the analyte and compared to standard for the output of the reagent deposit when irradiated in absence of the analyte. In this preferred system, the pyroelectric film will generate a voltage between electrodes. The difference in the voltages generated or the difference in voltage generated and the standard when no analyte present, will correspond to a concentration of the target analyte measured. In one aspect of the invention, the system 100 provides for the pyroelectric film transducer/reagent to be re-set or baselined. This means that, after a detection of the target substance and corresponding color change in the reagent, the reader stores voltage measured after the reagent is illuminated by a given LED. In this way, if a subsequent LED illumination does not result in a larger amount of heat being detected (i.e., because of no further colorimetric change in the reagent), the output signal may be recognized as the same as that received in the previous illumination, and thus the reader will not indicate erroneously that the target substance has again been detected. On the other hand, if additional exposure caused the reagent to further react colorimetrically, then the voltage measured would be different and the difference in voltage can be used to indicate the concentration detected. The output change is directly proportional or inversely proportional to the amount of the change on the reagent deposits upon exposure to the target analyte. Direct and inverse proportionality depend on the nature of the reagent deposits and the target analyte.

The above-described resetting or baseline method is just one example of a suitable method that allows the reagent to be repeatedly illuminated and exposed a plurality of times. In each case, the system 100 effectively stores in a memory the amount of heat (or corresponding voltage) that a reagent absorbs in response to an LED illumination. This allows the reagent to be reused, and be used longer in the field. This also allows the system to discriminate between different degrees of exposures. It is important to note, however, that the resetting or baselining described above requires the reagent to be non-reversible (does not revert back to its original color). The non-reversible reagent will have a maximum value of exposure at which point the reagent is totally consumed or saturated. At this point of maximum exposure, the reagent cannot be used to read any further exposures of analyte. The maximum total change of the reagent will be stored as a data value within either the memory chip on the reagent carrier or other memory such as the internal memory in the microprocessor. In the case of reversible reagents, the reagent will revert back to the original status in the absence of the target analyte. However, even the reversible reagent will have a maximum exposure point at which the reagent may be damaged and an expiration date that would be stored within the memory as described above.

In yet another aspect of the inventive testing method, a non-reversible reagent/pyroelectric film is used in combination with a continuously running pump. The pump is operated to continuously sample the local fluids environment while the LEDs of the reader is activated to illuminate intermittently. Whenever a target substance is detected, causing a colorimetric reaction and subsequent reading of the concentration detected, the reagent/pyroelectric film is reset or baselined. In this manner, the system 100 may be used for continuous monitoring in the field and multiple exposures.

FIG. 2 provides the basic structure of a carrier 40 for use with the system 100 according to the invention. The carrier 40 of FIG. 2 includes a plurality of colorimetrically reactive reagent deposits 32 deposited thereon. Different types of reagent deposits 32 may be selected such that one testing operation can detect a corresponding plurality of target substances. The reagent deposits 32 are preferably arranged in predetermined sets 32*a*. In one preferred embodiment, the system 100 includes a series of distinct reagent deposits 32 provided in the same set 32*a*, such that several target substances may be tested at the same time. Alternatively, a predetermined set 32*a* may consist of one reagent deposit (see e.g., FIG. 3*a*).

The carrier 40 further includes a pyroelectric film transducer 42 on which the reagent deposits 32 are deposited. The reagent deposits 32 may be deposited directly on the pyroelectric film transducer 42 using an ink jet printer or a screen print system. The pyroelectric film transducer 42 has a top surface 36 and a bottom surface 38. In embodiment of FIG. 2, the top and bottom surfaces 36, 38 provide the electrodes by which an electrical signal may be outputted from the carrier 40.

FIGS. 3*a*-3*c* depict a variation of a carrier 40 according to the invention. To facilitate description, the cartridge 40 of FIG. 3 is shown with only one reagent deposit 32. The reagent deposit 32 is contained or housed within an initially sealed tunnel 34, as best shown in end view of FIG. 3*b*. The tunnel 34 is essentially an elongated conduit extending the length of the cartridge 40 providing for fluid communication between the pump 10 and a local fluid environment. Preferably, the tunnel 34 also contains a filter 68 shown in FIG. 4. The tunnel 34 further includes an inlet end 34a and an outlet end 34b, which provides a conduit for passage of a sample of the local fluid environment. The inlet and outlet ends may be sealed by a plastic film or the like. As further described below, upon engagement of the cartridge 40 with the reader 62, the sealed inlet end 34a and outlet ends 34b are simultaneously punctured, thereby creating the fluid conduit and allowing for exposure of the reagent 32 to the local environment.

Referring to the end view of FIG. 3b, the pyroelectric film transducer 42 is provided as a mat situated along the bottom portion of the tunnel 34, thereby providing a bed or support for the reagent 32. In one variation of the cartridge 40, the cartridge 40 is made of glass such that the bottom surface on top surface of the tunnel is sealed by a glass surface. In further embodiments, the top end may be sealed by a plastic film.

Now referring to the bottom view of FIG. 3c as well, the carrier or cartridge 40 also includes an embedded memory chip 52 with leads or pins mateable with the reader 62. The memory chip 52 may be used to communicate the characteristics of the reagent dot 32 as well as the testing protocol or procedure for the target substance. The bottom view of FIG. 3c also shows lead lines 54 and connectors extending from the pyroelectric film. The connectors are situated so as to be mateable with corresponding connections on the piezoreader 60. Further, the cartridge 40 is also provided with a key/alignment hole or pin 56 for aligning the cartridge 40 with a corresponding hole or pin of the reader 62.

FIG. 4 shows the cartridge of FIG. 3 engaged within a receiving compartment or bay 66 of the flip top reading device 60. When properly situated in the compartment, as provided by aligning the key alignment hole with the corresponding key alignment pin of the reader, the connectors 54 for the pyroelectric film 42 and those for the memory chip 52 align with and connect with corresponding connections on the piezoreader 60. Moreover, the inlet and outlet ends of the tunnel 34 of the cartridge 40 align with corresponding conduits integrated with the reader 62. A tab device provided on the compartment may be positioned so as to puncture the inlet and outlet ends 34a, 34b. In this way, operation of the pump 10 draws a sampling of the local gaseous or fluid environment through the tunnel 34, thereby exposing the reagent 32 and initiating a colorimetric change therein. FIG. 4 also illustrates the use of a pump 10 having a pumping conduit 10a connecting the cartridge with the pump 10, and also with the sampling inlet 10b and outlet 10c.

The display 26, shown in FIG. 4 is a standard LCD display, and may be alpha-numeric or graphical depending on what information is necessary to display. The display 26 provides the user with a numeric indication of the measurement of the concentration of the target substance (either direct immediate exposure or long term dosimeter readings). The display 26 may also display text and graphics of alarms, menus for device settings including: alarm points; time; date, data-logging; analyte name; sensor name; filter name; parts numbers; software names and version; temperature; humidity; altitude; pressure; sampling time; operating instructions, sampling volume, serial number, lot number, expiration date, interferences, unit of measure, over range, minimum detectable limit, accuracy, sample flow, flow rate, number of exposures, location, designation, test operator identification, accessories names, developer names, reagent saturation, range, environment operation conditions and corrections factors, or any other information, data or the like necessary for operating the device.

The pump 10 may be a fan, air pump, or other device that is capable of moving a sample of the local environment. The pump may be located on either the intake air path before the reagent or located in the exiting air path. The pump 10 may be operated continuously or intermittently, or may be turned on for a specific amount of time for purposes of obtaining a reading or to minimize power consumption or until a specific volume of the local environment has been sampled. Alternatively, the pump may be known to operate at a specific flow rate to increase, decrease or otherwise vary the sample through conduit 34.

In the preferred embodiment of the invention, the pump 10 is used with a flow regulator 12. If the invention did not employ a flow regulator 12, the pump would be used as an uncontrolled fluid source that would indicate the presence of a fluid, but the measurement of the amount of the target fluid would not be as accurate as a measurement taken with a flow regulator 12. The flow regulator 12 can either use feedback from the motor or from the flow sensor 14. A preferred method is to control electrical power to the pump device with a feedback from the flow sensor. Such regulation may consist of controlling the pump speed and/or the on and off time of the pump in either a pulsed fashion or on for a specific time period. The flow regulator consists of an electric circuit that interfaces with the flow sensor 14 (or motor feedback) and provides power to the motor directly.

The inventors have discovered that the use of a pump 10 in combination with pyroelectric (and other) technology provides certain benefits. For example, the use of a pump speeds up the reaction time of the reagent and allows for a virtually instantaneous measurement of the level of the target substance in the local environment.

Furthermore, precise control of the pump, as in the present invention, provides measurements exceedingly more accurate than is achievable with prior art systems and methods. This achievement by the inventors stems from the understanding that the chemical, biochemical, biological, physical and/or molecular reaction of the reagent deposit is proportionally relevant to the amount of fluid, air or gas that is contacted with the reagent deposit surface. With prior art colorimetric reactions, the fluid, air or gas is contacted with the reagent through simple diffusion—which has to be timed in order to provide an acceptable, accurate measurement. In the present inventive system and method, the flow rate of the pump can be measured and/or controlled, as well as the pumping duration, and thus, the amount of fluid, air or gas contact with the reagent can also be measured and/or controlled. As a result, a high level of accuracy in measurements can be achieved and repeated. Moreover, use of the pump to initiate or encourage contact provides more precise measurements than the use of simple diffusion because the diffusion rate may be affected and varied by external conditions, including wind. The flow of the pump will either be controlled by an orifice, mechanical control, analog electronic feedback or digital electronic feedback. The method of measurement of motor speed could be accomplished by voltage, optical to electrical, electrical timing signal or measurement of the inlet flow versus outlet flow of the pump.

Alternatively, a measurement device may be used to measure the amount of sample delivered by the pump. If the pump 10 operates at a known flow rate, the measurement device could comprise of a timer which may be internal or external to the microprocessor to time the length of operation of the pump and a converter to convert the flow rate and the pump operation time to a volume of sample delivered. The flow sensor 14 may be provided as the optional measuring device to provide feedback to the flow regulator 12. The preferred method of flow sensing employs a differential pressure sensor. A wide range of sensors, including electromechanical sensors, hot wire sensors, optical sensors and many others can be used.

Further, the reader 62 preferably includes a circuit board or other support 70, which includes the reader 60, as well as the control mechanism 22. When the cartridge 40 is received in the bay 66, it is situated over the board 70, and such that LED's provided on the board advantageously align with the reagents 32. In further embodiments, multiple LED's of various wavelength maxima (e.g., colors) may be employed in combination with a light pipe or fiber optic conduit for selectively irradiating the reagent with a variety of light sources. The board 70 also includes contacts for the memory chip 52 such that reagent information and testing requirements may be communicated to the reader 62.

FIG. 5 depicts yet another reader 162 and carrier 140 combinations, according to the invention. The carrier 140 is shown being disengaged or detached from the receiving bay 166 of the reader 162. The carrier 140 includes one or more containers 110, each containing a set of reagent deposits 132. Preferably, the container 110 is a channel that is particularly adapted to fluidly communicating the local environment with the selected set of reagent deposits 132.

In one embodiment, the carrier 140 may be fed into the reader 162 by an electric motor. In another embodiment, the carrier 140 may be fed through operation of some type of ratchet or manually fed by hand. The carrier 140 could be made of a firm, durable plastic and may contain a barcode, magnetic stripe or embedded memory chip or bar code to identify the specific carrier 40 and the target analytes, the ranges it is capable of detecting, and other information.

The system further includes a means for selecting or designating a predetermined set of reagent deposits 132 for exposure to the sample containing the target substance. In this manner, the user selects a specific reagent deposit to test for a target substance. Upon engagement of the carrier 140 with the reader 162, the selecting means penetrates the container 110 containing one set of reagent deposits, thereby exposing the selected reagent deposits to the local environment, as further discussed below.

The system 100 embodies a reagent deposit 132, which due to its limited quantity is easily and quickly reacted upon exposure to air and humidity, causing a short "shelf life." In another embodiment, each container 110 containing a set of reagent deposits 132 is covered by a shield 130, shown in FIG. 5 as a tunnel, to shield the reagent deposits 132 from the local environment until the carrier 140 is engaged with the reader 162. Upon engagement of the carrier 140 with the reader 60, the shield of the selected set of reagent deposits 132 is penetrated or compromised, allowing exposure of the selected set of reagent deposits 132 to the local environment containing the target substance. The tunnel is preferably made of glass, but could also be made of another rigid material such as Mylar or polyvinyl chloride. The ends of the tunnel are preferably covered with film that may be compromised or punctured to expose the container 110. Alternatively, the shield 130 could consist of a film covering each container 110. In one aspect of the invention, the shields (either in the form of a film covering or a tunnel) allow for multiple testing procedures using the same carrier 140. During a testing operation only the selected set of reagent deposits 132 are exposed, leaving the remaining sets of reagent deposits unexposed beneath the shield. The shield-compromiser preferably consists of a sharp implement to puncture the film-covered ends of the tunnel or the film.

In another embodiment of the invention, a filter is used to filter out interferences from the local environment containing the target substance before the local environment comes in contact with the selected set of reagent deposits. The filter may comprise a variety of materials and coatings to specifically filter interferences (through membranes that restrict particle size, chemicals that react with, remove, or change a chemical compound into another chemical that will not interfere with the target analyte) from the selected set of reagent deposits. Filters remove undesirable substances through adsorption, absorption, chemical reaction, biochemical reaction, biological, and/or molecular interaction. The filters may have the shape of porous numbers, liquid or solid encapsulated or porous solid supports. The filters may, in the alternative, be in the form of a chromatography column with filtering media coated on the inside walls. The sample environment, including the undesirable particulates, is passed through the column along the coated walls, and fractionally separates. Because of the temporary nature of chromatographic columns, this type of filter is preferably for use with portable type systems. This type of filter has the advantage of temporarily holding back the interfering substance during measurement of the primary target chemical, but then allows for measurement of the interfering substance when heat is applied (and release of the interfering substance). Specific filters could include a hydrophobic filter to remove humidity, a filter to screen out toluene and xylene from benzene and air, a filter to remove chlorine gas from a mixture of chlorine dioxide and air, a filter to absorb or adsorb water vapor and many others. The filters may be reversible, nonreversible, reusable and nonreusable.

These filters may be used individually or in combination as needed to filter interferences from the selected set of reagent deposits 132. Further uses of such filters will be apparent to one skilled in the art upon review of the present disclosure.

Like the pump, the filters can be engageable with the container 110 containing the selected set of reagent deposits. The filters could optionally be stamped with a bar code such that they may be recognized by the reader 162 with a barcode reading device. This would allow the reader 162 to compensate, or report to the user the use of the filter or the lack of presence of the filter. Furthermore, the filters could optionally be constructed in such a manner that the filter itself would contain or be made of a colorimetric substance that would cause a color change of the filter material showing that the material is being consumed or that it has been fully consumed or the rate at which it is being consumed.

As previously mentioned, the cartridge is mateable with and then detachable from the reading apparatus. When keyably engaged with the reading apparatus, the air channel, flow path cartridge channel, and outlet are fluidly aligned so as to allow for the passage of pumped fluid or air therethrough. Alternatively, the reading apparatus may be equipped with a key or piercing mechanism for piercing film sealably applied to the ends of the cartridge channel. Thus, upon proper receipt of the cartridge in the cartridge bay, the reagent deposits may be exposed with fluid sample from the local environment. Accordingly, detection and indication of the target fluid can occur immediately.

One way for the unit to "open" or "pierce" the cartridge is for the unit to contain two hollow pins which are sufficiently long to puncture the bottom of the cartridge at each end providing fluid path though the puncture pins themselves. Due to the possible manufacturing difficulty of puncturing the cartridge, one preferred method of cartridge construction would entail a cartridge as shown in FIGS. 3-5. This would be the composite of two plastic plates that, when joined together form a "credit card" shaped plastic device with a hollow interior forming a tunnel or channel through the middle of the device. Prior to assembly of the opposing halves of the cartridge, the embedded pieces would be placed inside the device, then both pieces would be assembled and sealed possibly with a heat seal, sonic weld, a glue or the like.

Figure 6:
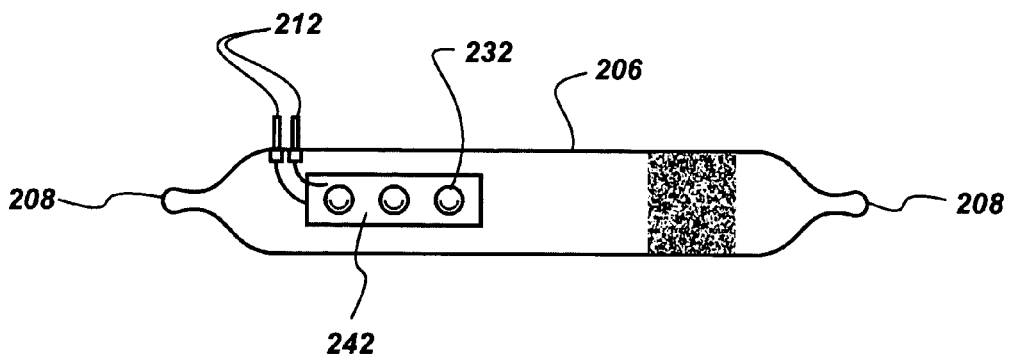
FIG. 6 is a simplified diagram of a detector tube according to the invention.

FIG. 6 depicts yet another embodiment of the invention. In this embodiment, a detector tube 206 is employed to support the carrier 40 during storage and testing. The detector tube 206 is a hermetically sealed glass tube, structurally similar to those commercially available in the industry. The detector tube has a breakable inlet end 208a and a breakable outlet end 208b. The carrier of FIG. 6 includes three reagents spots 232 supported on a pyroelectric film transducer 240. The carrier further includes two wire lead lines 212 that are directed through the walls of the glass tube, thereby providing two electrical connections for use with a reader. The detector tube 206 may also house a layer of LED(S) positioned adjacent or beneath the carrier so as to be operable for irradiation of the reagents. In the alternative, the LED layer may be positioned outside of the detector tube 206 and incorporated with the reader.

Figure 7A:
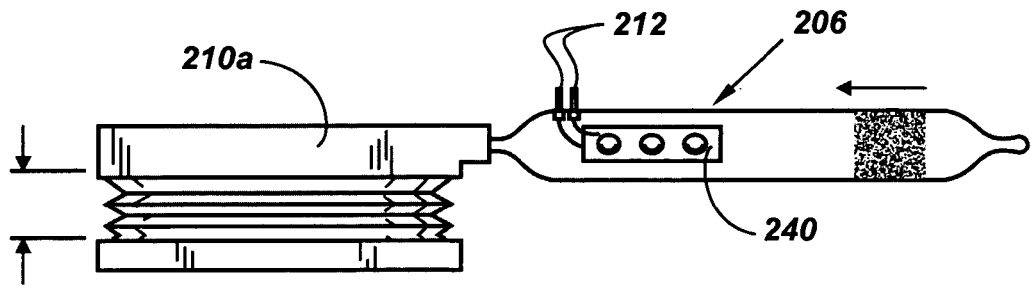
FIG. 7A is a simplified diagram of the detector tube of FIG. 6 engaged with a pump, according to the invention.
Figure 7B:
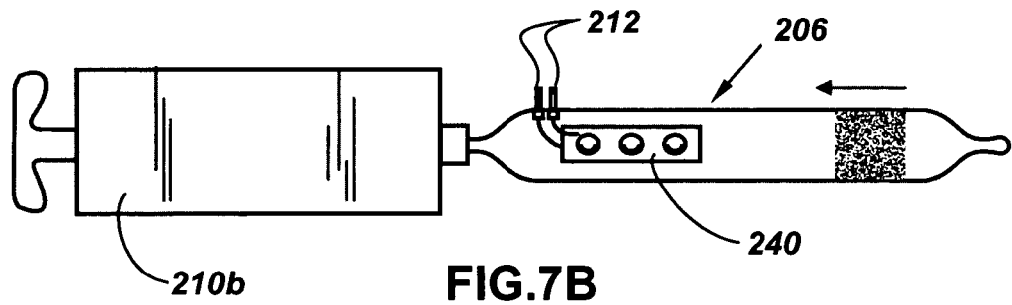
FIG. 7B is a simplified diagram of the detector pump of FIG. 6 engaged with a second type of pump, according to the invention.

FIGS. 7A and 7B depict the detector tube 206 operated with a bellows pump 210a and a manual pump 210b. Either pump may be used in combination with the detector tube 206 to conduct a field-testing operation. In particular, the detector tube ends are broken and inserted or engaged with the pump, thereby drawing a sampling of the environment through the detector tube and past the reagent. Thus, if the reagent is exposed to the target substance, a colorimetric change occurs. The detector tube is then disengaged from the pump and engaged with the appropriate reader such that the connections 212 mate with corresponding connections in the reader. Upon engagement with the reader, one or more LEDS on the reader may be operated to irradiate the reagent.

Figure 8A:
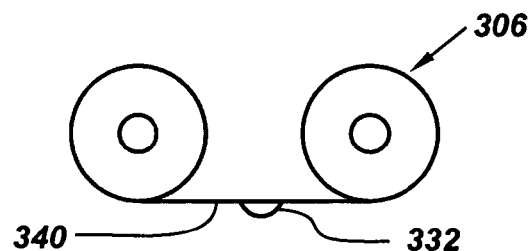
FIG. 8A is a simplified diagram of a third carrier suitable for use with the system.
Figure 8B:
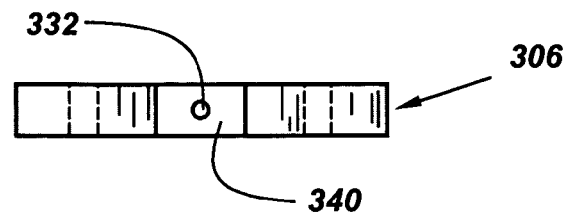
FIG. 8B is simplified plan view of the carrier in FIG. 8A.

FIGS. 8A and 8B depict yet another variation of a carrier for use with the system according to the invention. In particular, FIG. 8 depicts the use of a reel-to-reel tape mechanism 306 for sealingly storing and dispensing individual carriers 340. As shown in FIG. 8B, the reel tape may be segregated into distinct sections, including a section comprising a carrier 340. The carrier will include pyroelectric film transducer 340 and one or more reagent deposits 332 thereon. Conveniently, the tape acts to seal the reagent 332 before the reagent 332 is exposed during unwinding, thereby eliminating the need for a sealed container or tunnel. Accordingly, one benefit of the embodiment of FIGS. 8A, 8B is that it allows for "long term" measurement, while preserving the life of the unused reagents.

The roll of tape may include various combinations of reagents or only one type of reagent. Further, the reel-to-reel mechanism may be mounted or housed integrally with a reading device. In the alternative, the reel-to-reel mechanism may be integrated with a fixed testing mechanism rather than a field deployable portable gas detector.

Figure 9:
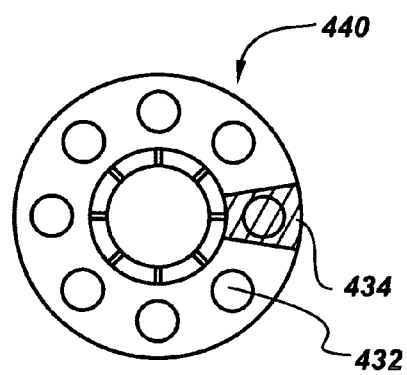
FIG. 9 is a simplified diagram of a fourth carrier suitable for use with the system.

FIG. 9 depicts yet another variation of a carrier for use with the system according to the invention. The carrier of FIG. 9 is a disk type carrier 440 preferably holding a plurality of reagent deposits 432. The reagent deposits 432, as before, will be deposited on and supported by a mat of pyroelectric film 442. The pyroelectric film 442 may be individual mats or a continuous, circular sheet of film, as shown in FIG. 9. The bay 66 of reader 62 may be modified to accommodate either of carriers 340 or 440 for use.

FIG. 9 also illustrates a reagent deposit sealingly situated in a tunnel 434. The tunnel 434 includes fluid communication inlets (not shown) and outlets, (not shown) which are penetrated and unsealed upon engagement of the disk carrier 440 with the appropriate reader. For example, in FIG. 9, only one reagent deposit remains unsealed, but is positionally engaged with the reader so as to be in alignment with the pumping means provided by the reader. When aligned and in operation, the pump may be operated to draw air from the periphery of the tunnel and past the reagent, towards the center of the disk carrier 440. Upon conclusion of a testing operation, the disk carrier 440 may be rotated so as to align yet another reagent deposit for a subsequent operation. As before, the tunnel 434 may be covered by glass or film, with the ends preferably covered by a puncturable or penetrable film sheet.

Figure 10:
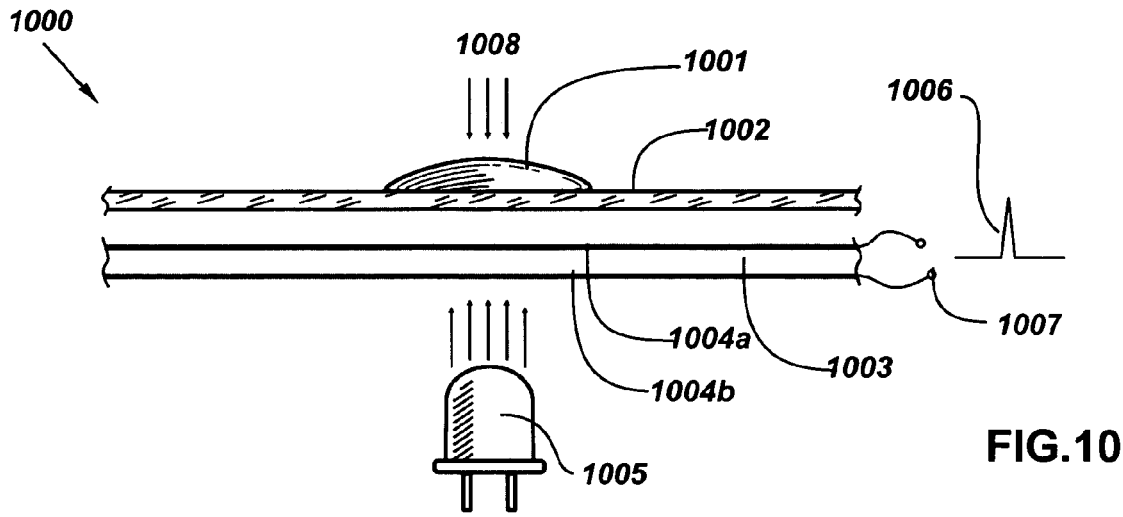
FIG. 10 is a simplified diagram of a basic detection system according to the basic system incorporating a pyroelectric film and an EM electromagnetic spectrum emitting source, according to the invention.

FIG. 10 depicts an alternative arrangement for the system of detecting a target analyte utilizing pyroelectric technology, according to the invention. The system 1000 includes at least one reagent deposit 1001 supported on a transparent substrate 1002. The transparent substrate 1002 may be glass or plastic such as polyester, polypropylene or PVC. The reagent 1001 is formulated, coated, impregnated and/or deposited on the substrate 1002 under reduced pressure or vacuum so as to prevent bubbles from being retained within the reagent 1001. The substrate 1002 is positioned adjacent a piezoelectric or pyroelectric film 1003 having a top metallic conductive film surface 1004a and a bottom conductive film surface 1004b. The piezoelectric or pyroelectric film may be comprised of polivinylidine fluoride (PVDF) material. The top conductive film surface 1004a is spaced directly apart from the transparent substrate 1002 as shown in FIG. 1.

FIG. 10 depicts an alternative arrangement for the system of detecting a target analyte utilizing pyroelectric technology, according to the invention. The system 1000 includes at least one reagent deposit 1001 supported on a transparent substrate 1002. The transparent substrate 1002 may be glass or plastic such as polyester, polypropylene or PVC. The reagent 1001 is formulated, coated, impregnated and/or deposited on the substrate 1002 under reduced pressure or vacuum so as to prevent bubbles from being retained within the reagent 1001. The substrate 1002 is positioned adjacent a piezoelectric or pyroelectric film 1003 having a top metallic conductive film surface 1004a and a bottom conductive film surface 1004b. Elements 1004a and 1004b are collectively represented as element 1004. The piezoelectric or pyroelectric film may be comprised of polivinylidine fluoride (PVDF) material. The top conductive film surface 1004a is spaced directly apart from the transparent substrate 1002 as shown in FIG. 1.

Figure 11:
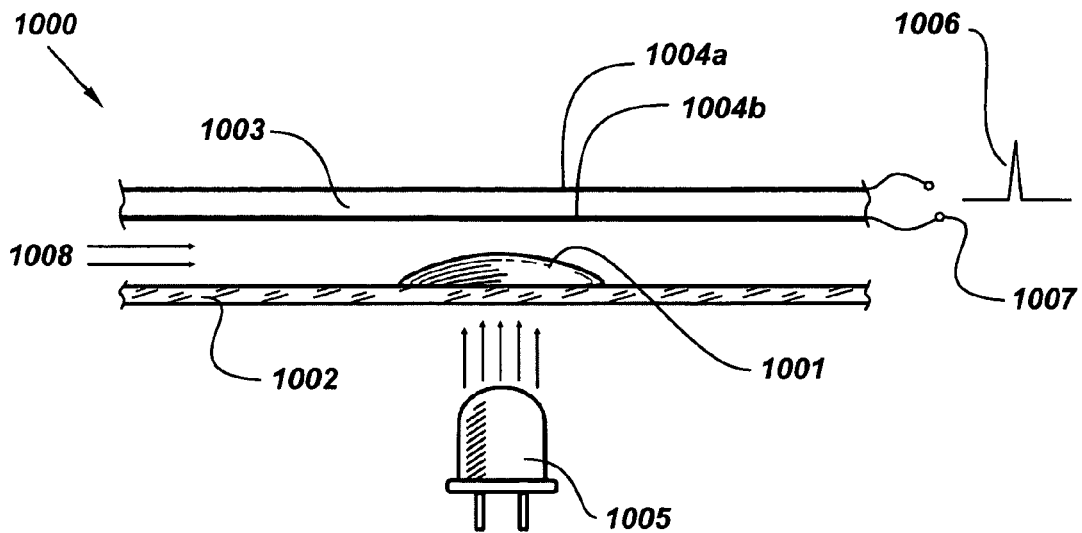
FIG. 11 is a simplified diagram of an alternative detection system incorporating a pyroelectric film and electromagnetic spectrum emitting source, according to the invention.

In FIG. 11, the reagent deposit 1001 is supported on the transparent substrate 1002, but the transparent substrate 1002 is positioned below the pyroelectric film 1003. Moreover, the EM source 1005 is positioned below the transparent substrate 1002, and is operable to direct energy towards and through the transparent substrate 1002. In this particular arrangement, the direction of fluid flow 1008 is provided in between the transparent substrate 1002 and the pyroelectric film 1003. Furthermore, the pyroelectric film 1003 is positioned above and spaced apart from the reagent deposit 1001 to detect energy absorbed by the reagent 1001.

Figure 12:
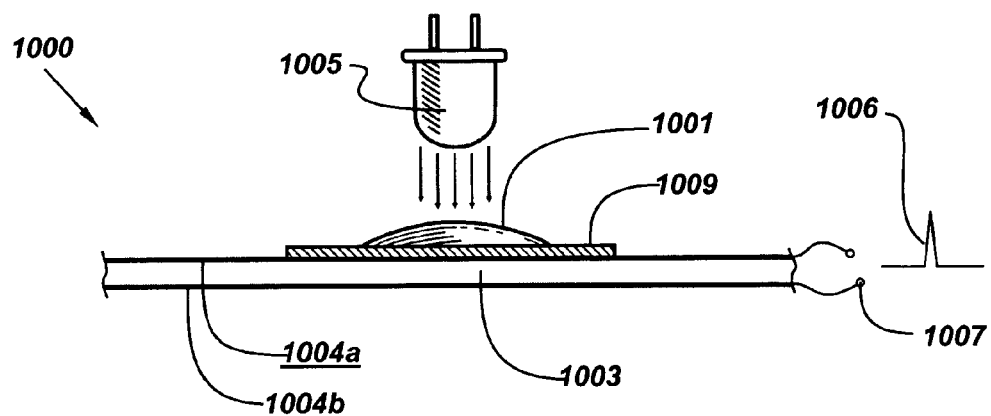
FIG. 12 is a simplified diagram of yet another detection system incorporating a pyroelectric film and electromagnetic spectrum emitting source, according to the invention.

In the alternative arrangement of FIG. 12, the reagent deposit 1001 is deposited directly on an electrically conductive film 1009. The conductive film 1009 may be thin metal film or metallized plastic. In turn, the electrically conductive film 1009 is supported directly on the pyroelectric film 1003, and more specifically, directly on the conductive film surface 1004a. Thus, the pyroelectric film 1003 can detect energy changes in the reagent deposit 1001 by way of the electrically conductive film 1009 by mere physical contact.

Figure 13:
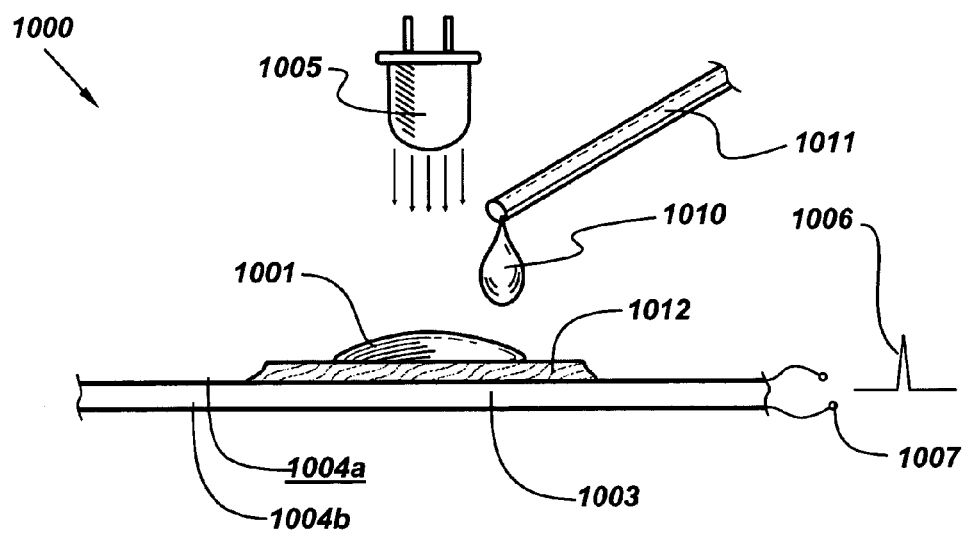
FIG. 13 is a simplified diagram of yet another detection system incorporating a pyroelectric film and electromagnetic spectrum emitting source, according to the invention.

In the arrangement illustrated in FIG. 13, the reagent 1001 is deposited on a thermally conductive paste 1012 that is supported on the pyroelectric film 1003. Further, the thermally conductive paste 1012 is supported directly on the pyroelectric film 1003, and more particularly, on the top conductive film surface 1004a. As in FIG. 12, the EM source 1005 is positioned above the reagent deposit 1001. A suitable thermally conductive paste 1012 is a conductive polymeric or inorganic metallized paste. Operation of the illustrated system further requires the use of a pipette, dropper and/or applicator 1011 to communicate additional reagent and/or developer 1010 onto the reagent deposit 1001. This is needed as some reagents deposits require addition of other reagent(s) before and/or after sampling to activate or to react with the reagents deposits and/or the fluid analyte(s) to enable the desired detection response upon exposure to the fluid analyte(s).

Figure 14:
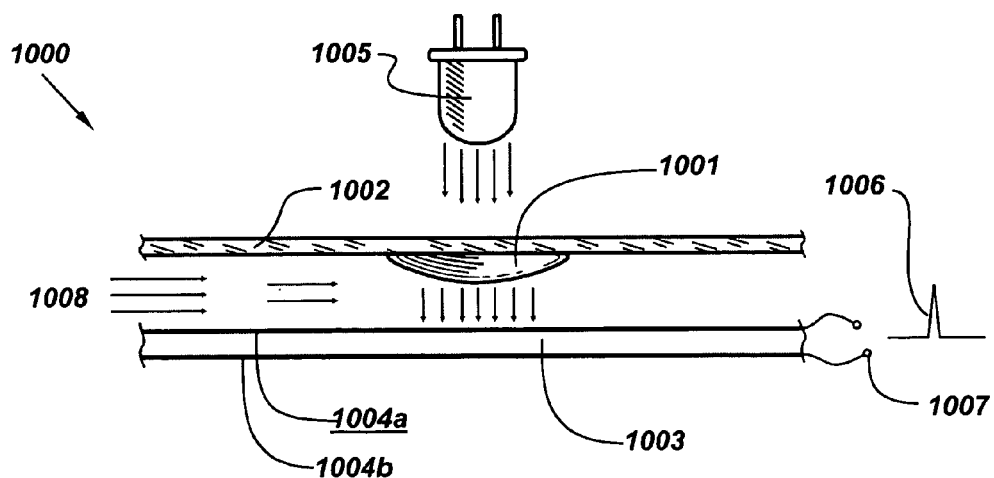
FIG. 14 is a simplified diagram of yet another detection system incorporating a pyroelectric film and electromagnetic spectrum emitting source, according to the invention.

Now turning to FIG. 14, an alternative arrangement is shown wherein the reagent deposit 1001 is positioned on to a bottom side of the transparent substrate 1002. As further shown, the pyroelectric film 1003 is positioned below and spaced apart from the transparent substrate 1002. In this way, the sample fluid flow direction 1008 is moved between the transparent substrate 1002 upon which reagent deposit 1001 is deposited and the pyroelectric film 1003. Moreover, the EM source 1005 is preferably positioned above the transparent substrate 1002, so as to direct energy towards and through the transparent substrate 1002 and then to reagent deposit 1001.

FIGS. 15-19 illustrate yet further alternative arrangements for the system 1000 according to the invention. In each of these arrangements, the system 1000 employs at least two EM sources 1005 to direct energy towards the reagent deposit 1001. In the arrangement shown in FIG. 15, an EM source 1005 is positioned both above and below the pyroelectric film 1003. The use of a pair of EM sources 1005 provides for intensification of the electromagnetic spectrum that is irradiated on the reagent deposit 1001. As a result, the sensitivity of the system is increased to yield more precise detection of target analytes.

Figure 15:
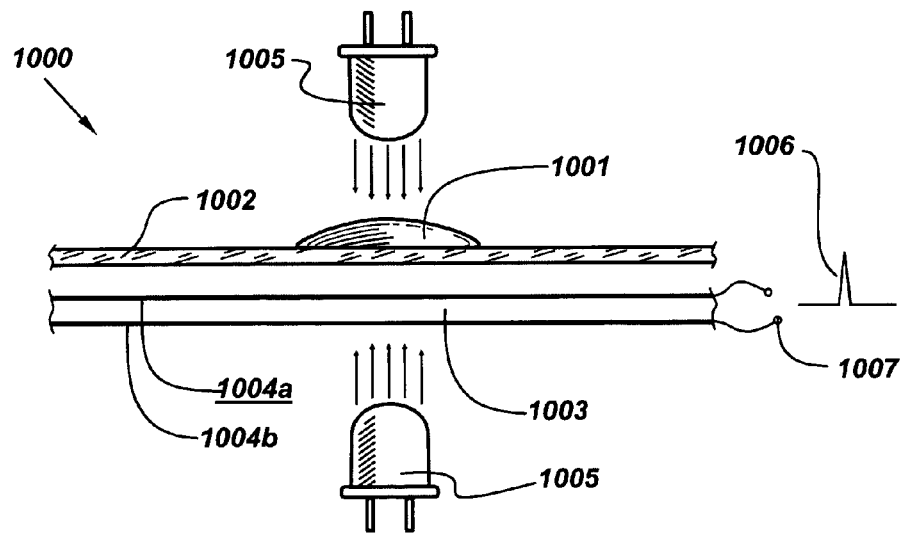
FIG. 15 is a simplified diagram of yet another detection system incorporating a pyroelectric film and a plurality of electromagnetic spectrum emitting sources, according to the invention.

In FIG. 15, the reagent deposit 1001 is deposited on a transparent substrate 1002, which is positioned above and spaced apart from pyroelectric film 1003. The pyroelectric film 1003 further includes a top metallic conductive surface 1004a and a bottom metallic conductive surface 1004b. The conductive surfaces 1004 connect to a pair of electrodes 1007, which, during operation, generates electric signals 1006 that correspond to the measurement of the energy (i.e., energy change) retained or embodied in reagent deposit 1001.

Figure 16:
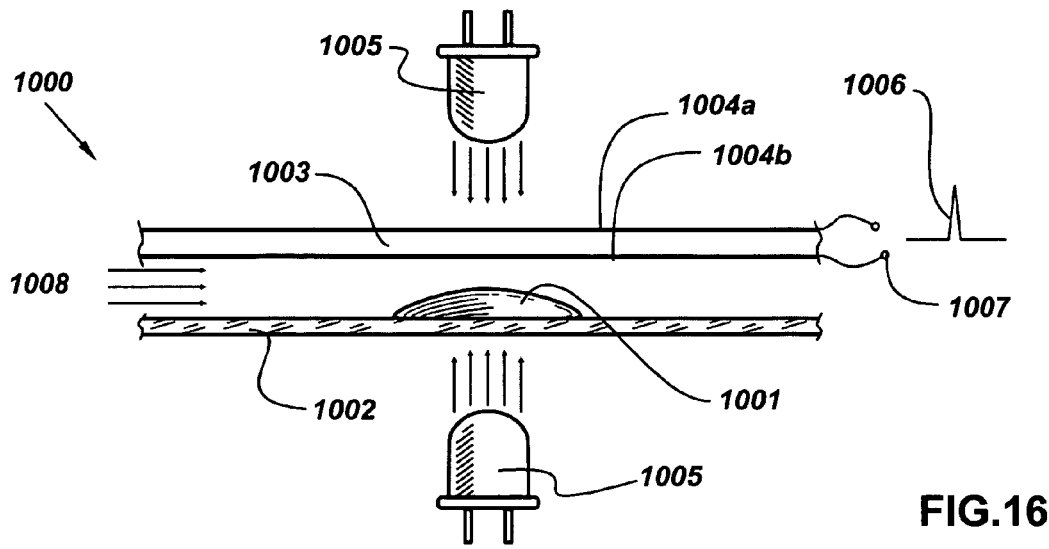
FIG. 16 is a simplified diagram of yet another detection system incorporating a pyroelectric film and a plurality of electromagnetic spectrum emitting sources, according to the invention.

In the alternative arrangement of FIG. 16, the reagent deposit 1001 is supported on transparent substrate 1002, which is positioned below the pyroelectric film 1003. In this way, the reagent deposit 1001 is between the two film surfaces 1003, 1002, and in the direction of flow 1008 therebetween. Again, as in FIG. 15, an EM source 1005 is positioned above and below the reagent deposit 1001, and more specifically, above the pyroelectric film 1003 and below the transparent substrate 1002. In this way, the intensity of the EM energy directed upon reagent deposit 1001 is intensified, thereby increasing the sensitivity of the inventive system.

Figure 17:
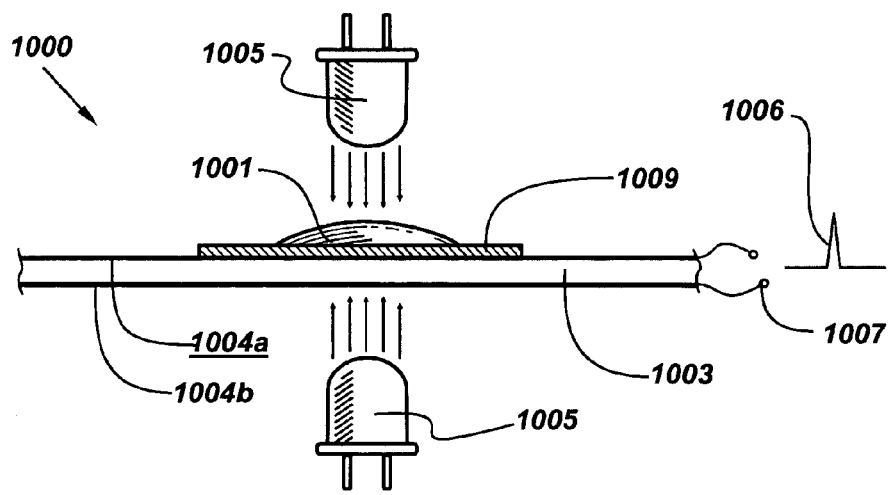
FIG. 17 is a simplified diagram of yet another detection system incorporating a pyroelectric film and a plurality of electromagnetic spectrum emitting sources, according to the invention.

Referring now to the alternative arrangement illustrated in FIG. 17, the reagent deposit 1001 is supported directly on an electric conductive film 1009. Further, the electrically conductive film 1009 is supported directly on the pyroelectric film 1003. As with the previously described embodiments, the pyroelectric film 1003 has a top metallic conductive surface 1004a and a bottom metallic conductive surface 1004b. Again, an EM source 1005 is positioned both above and below the reagent deposit, thereby intensifying the EM energy irradiated upon the reagent deposit 1001. In this way the sensitivity of the inventive system 1000 is also increased.

Figure 18:
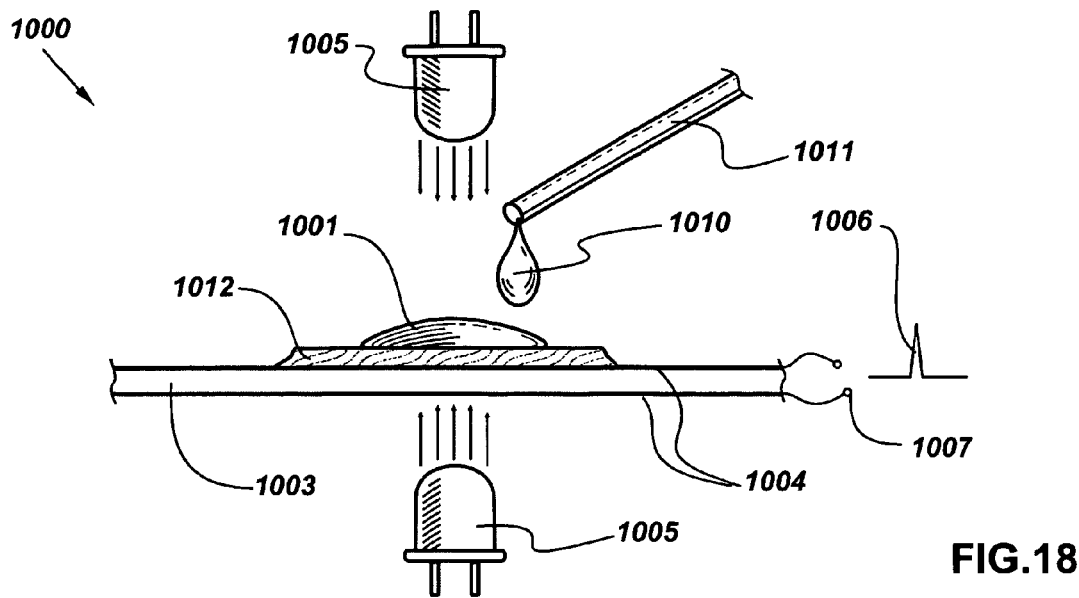
FIG. 18 is a simplified diagram of yet another detection system incorporating a pyroelectric film and a plurality of electromagnetic spectrum emitting sources, according to the invention.

In the system 1000 of FIG. 18, the reagent deposit 1001 is deposited on a thermally conductive paste 1012, which is supported on the pyroelectric film 1003. The EM sources 1005 are positioned above and below the reagent. The embodiment of FIG. 18 illustrates the use of an additional reagent and/or plurality of reagents and/or developer 1010 which are to be added prior to and/or after a sampling operation by way of applicator 1011.

Figure 19:
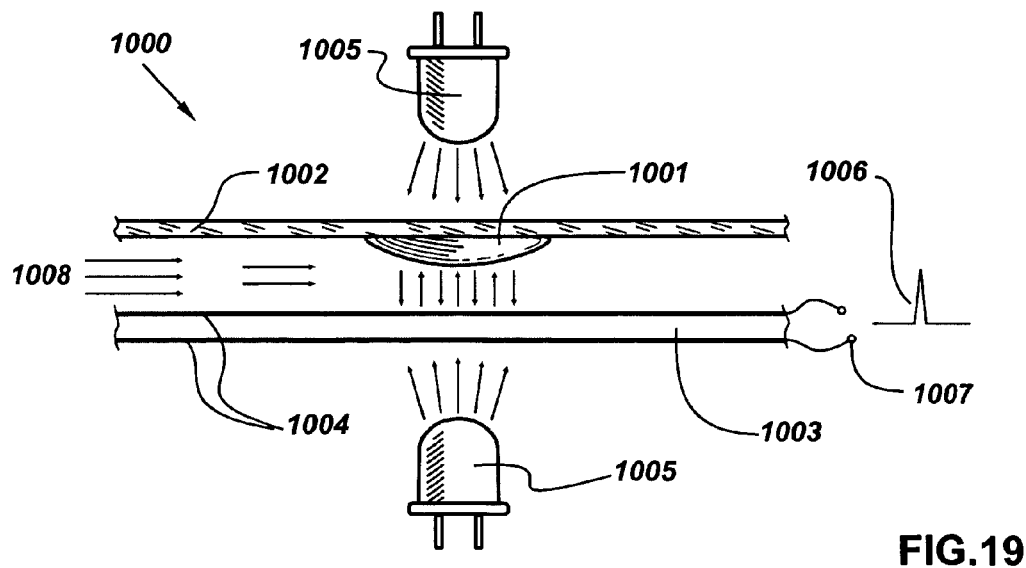
FIG. 19 is a simplified diagram of yet another detection system incorporating a pyroelectric film and a plurality of electromagnetic spectrum emitting sources, according to the invention.

In the system 1000 of FIG. 19, the transparent substrate 1002 supports a reagent deposit 1001 on a bottom surface, and the transparent substrate 1002 is spaced above and apart from pyroelectric film 1003. Then, an EM source 1005 is positioned both above the transparent substrate 1002 and below the pyroelectric film 1003. In this way, the sample flow 1008 is directed between the transparent substrate 1002 and the pyroelectric film 1003.

Figure 20:
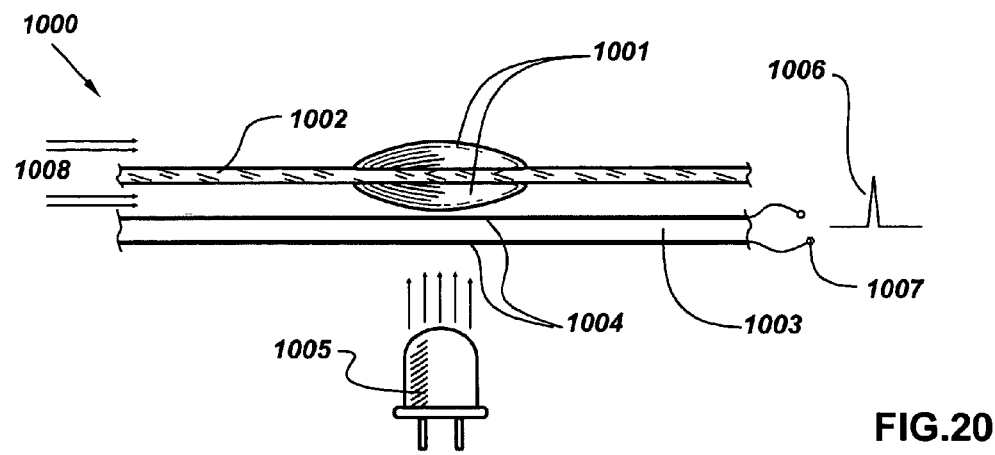
FIG. 20 is a simplified diagram of a detection system incorporating a pyroelectric film, an electromagnetic spectrum emitting source, and a plurality of reagents, according to the invention.

FIGS. 20-23 illustrate alternative arrangements of the inventive system 1000, wherein a plurality of reagent deposits 1001 are employed. Further, FIGS. 24-31 illustrate alternative arrangements wherein a plurality of EM sources 1005 is employed in conjunction with the plurality of reagent deposits 1001. In FIG. 20, a reagent deposit 1001 is deposited on both top and bottom surfaces of transparent substrate 1002, and at locations in generally vertical alignment (i.e., the position of the reagent deposits 1001 correspond to one another on opposite sides of the substrate 1002). This system 1000 provides for a sample flow 1008 above the transparent substrate 1002, and in between the transparent substrate 1002 and the pyroelectric film 1003. This arrangement also provides two locations wherein reactions between the reagent 1001 and the target analyte can occur. In this particular embodiment, the EM source 1005 is positioned below both the transparent substrate 1002 and on the other side of and below the pyroelectric film 1003. At this position, the EM source 1005 can direct EM energy through the pyroelectric film 1003, then through a reagent deposit 1001 and the transparent substrate 1002, in order to reach the second reagent deposit 1001.

Figure 21:
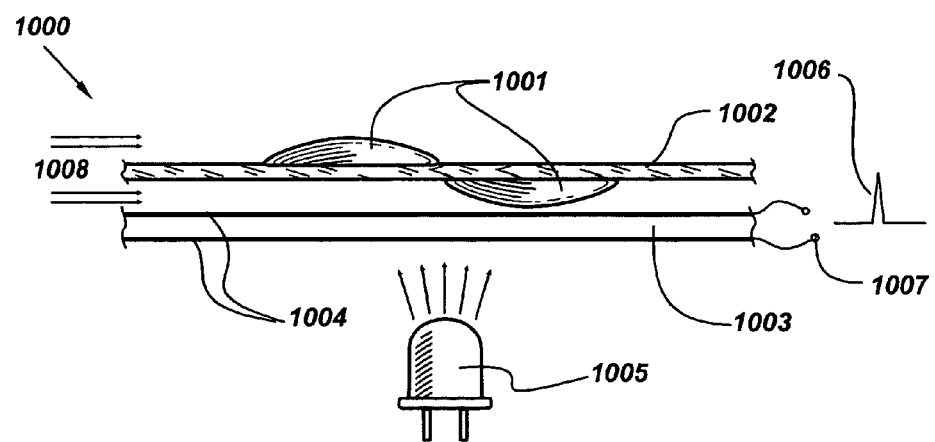
FIG. 21 is an alternative embodiment of a detection system incorporating a pyroelectric film, an electromagnetic spectrum emitting source, and a plurality of reagents, according to the invention.

In the arrangement depicted in the system 1000 of FIG. 21, the reagent deposits 1001 are again provided on opposite sides (above and below) the transparent substrate 1002. In this particular embodiment, the reagent deposits 1001 are not positioned, however, at locations that are vertically aligned on opposite sides of the transparent substrate 1002 (as in FIG. 20). In this way, the EM source 1005 directs EM energy through the pyroelectric film 1003 and through the transparent substrate 1002, in order to reach the top reagent deposit 1001 (i.e., bypassing the bottom reagent deposit 1001).

Figure 22:
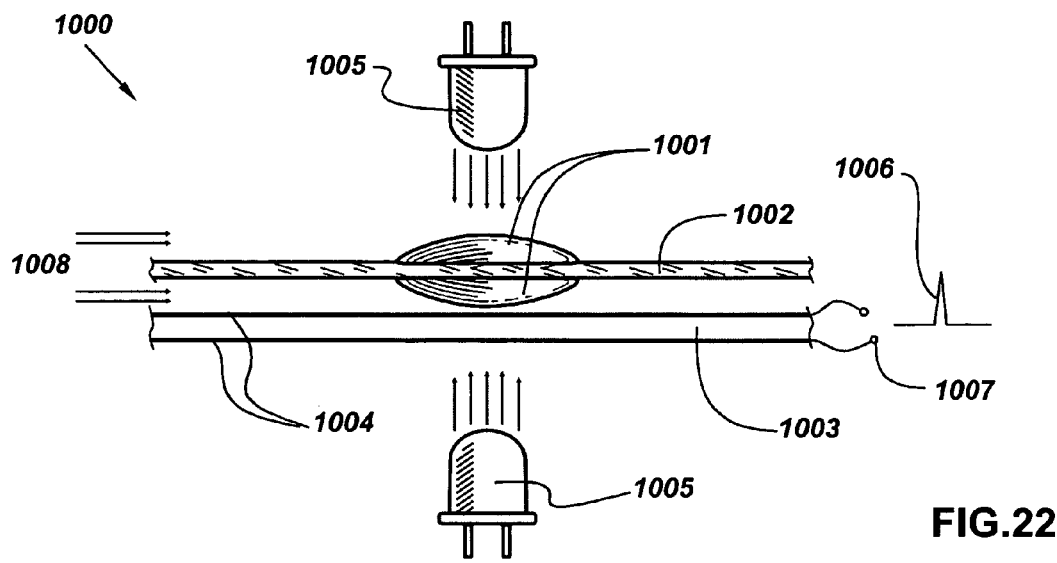
FIG. 22 is an alternative embodiment of a detection system incorporating a pyroelectric film, a plurality of electromagnetic spectrum emitting sources, and a plurality of reagents, according to the invention.

Now referring to FIG. 22, the arrangement illustrated therein utilizes a pair of reagent deposits 1001 located on opposite sides of the transparent substrate 1002. The reagent deposits 1001 are vertically aligned. Further, the arrangement includes a pyroelectric film 1003 positioned below and spaced apart from the transparent substrate 1002. In this arrangement, the system 1000 further includes a pair of EM sources 1005 positioned above the transparent substrate 1002 and below the pyroelectric film 1003. The bottom EM source 1005 is operable to direct EM energy through the pyroelectric film 1003 and to the bottom reagent deposit 1001. The top electrode 1005 is positioned above the top reagent deposit 1001 to direct energy directly into the reagent deposit 1001.

Figure 23:
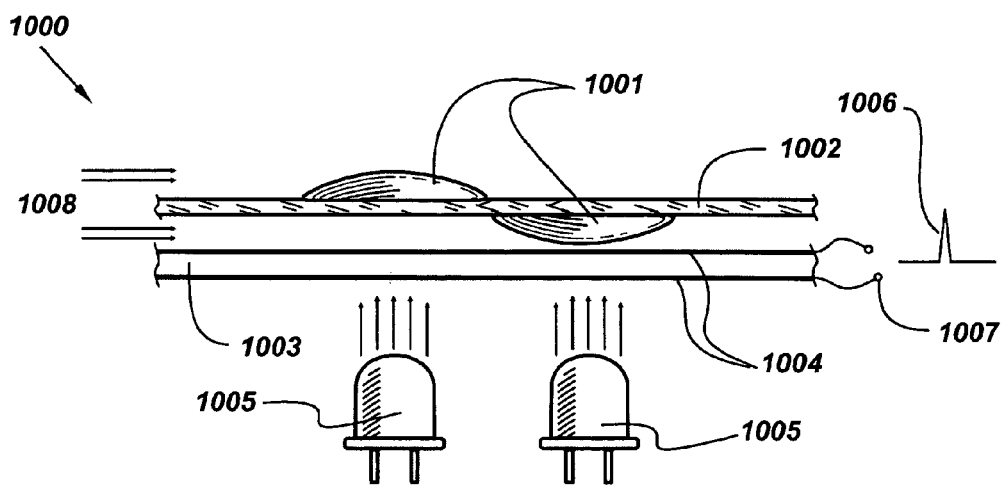
FIG. 23 is an alternative embodiment of a detection system incorporating a pyroelectric film, a plurality of electromagnetic spectrum emitting sources, and a plurality of reagents, according to the invention.

The system 1000 illustrated in FIG. 23 provides yet another variation of the invention. In this particular arrangement, reagent deposits 1001 are positioned above and below the transparent substrate 1002, but are not vertically aligned. In the operation of the system, EM energy is directed from below the pyroelectric film 1003, through the pyroelectric film, and towards the transparent substrate 1002. In this particular arrangement, a pair of EM sources 1005 are both positioned below the pyroelectric film 1003, each of which is in general vertical alignment with one of the reagent deposits 1001. Thus, in respect to the arrangement depicted in FIG. 23, the left most EM source 1005 directs energy through the pyroelectric 1003, through the transparent substrate 1002, in order to reach the top reagent deposit 1001.

Figure 24:
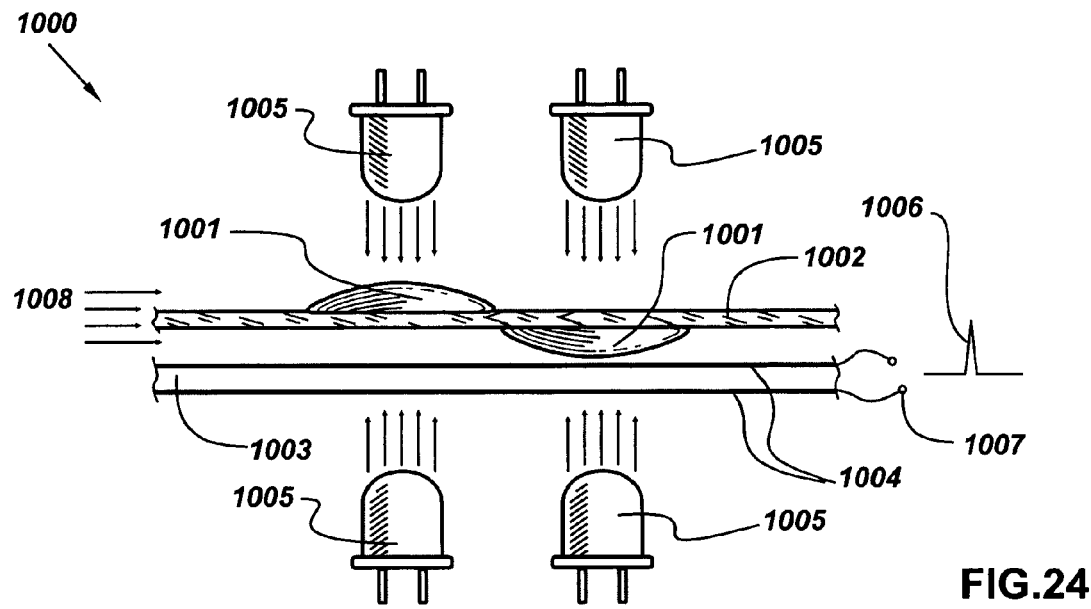
FIG. 24 is an alternative embodiment of a detection system incorporating a pyroelectric film, a plurality of electromagnetic spectrum emitting sources, and a plurality of reagents, according to the invention.

The system 1000 illustrated in FIG. 24 is a further variation of the system 1000 in FIG. 23. In this particular arrangement, a second pair of EM sources 1005 are positioned above the transparent substrate 1002. This system 1000 provides EM sources 1005 that can direct EM energy to each of the reagent deposits 1001 from both below and above the transparent substrate 1002.

Figure 25:
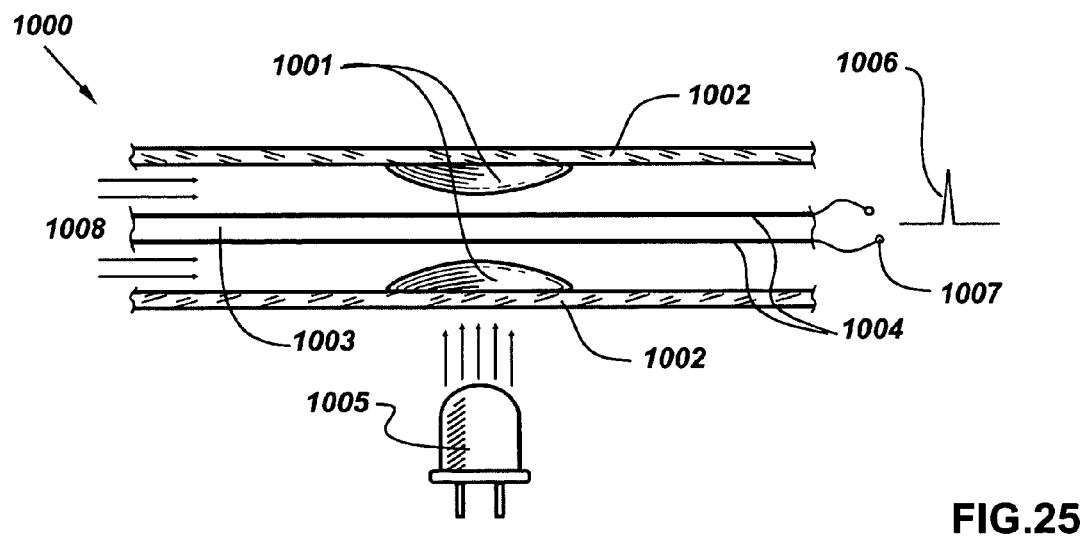
FIG. 25 is an alternative embodiment of a detection system incorporating a pyroelectric film, an electromagnetic spectrum emitting source, and a plurality of reagents, according to the invention.
Figure 26:
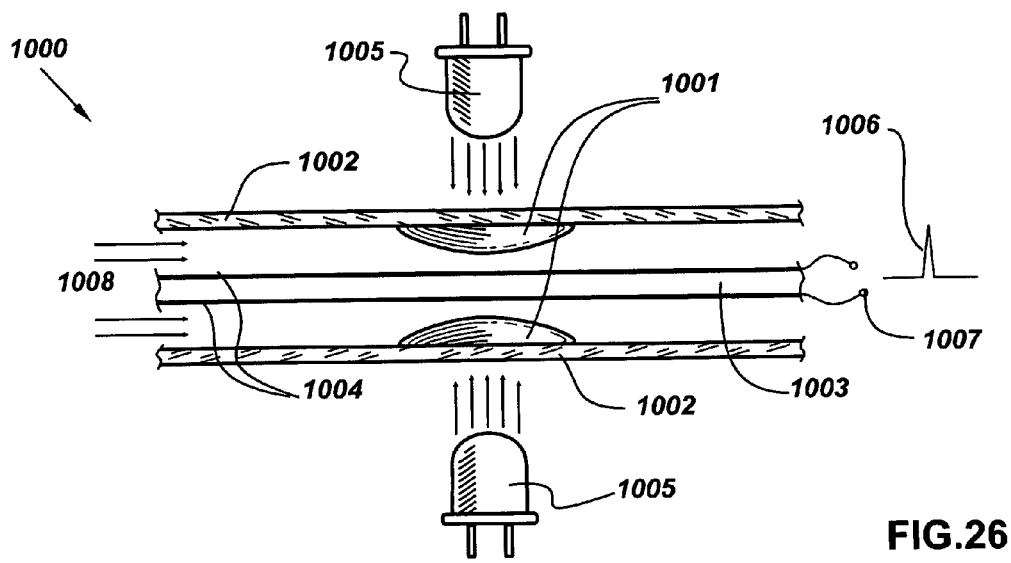
FIG. 26 is an alternative embodiment of a detection system incorporating a pyroelectric film, an electromagnetic spectrum emitting source, and a plurality of reagents, according to the invention.

FIGS. 25 and 26 each illustrates yet another alternative arrangement according to the invention, wherein two transparent substrates 1002 are employed. Specifically, a transparent substrate 1002, having a reagent deposit 1001 supported thereon, is spaced apart above and below the pyroelectric film 1003. In this way, two sample fluid flows 1008 are created between the pyroelectric film 1003 and each of the transparent substrate 1002. In these arrangements, the top transparent substrate 1002 supports the reagent deposit 1001 on a bottom surface and is spaced apart from the pyroelectric film 1003. Further, an EM source 1005 is positioned below the bottom transparent substrate 1002. The EM source 1005 is operable to direct EM energy through the bottom transparent substrate 1002 to reach the bottom reagent deposit 1001, and further, through the bottom reagent 1001, and the pyroelectric film 1003 in order to reach the top reagent deposit 1001.

In the arrangement of FIG. 26, a second EM source 1005 is positioned above the top transparent substrate 1002. In this way, each reagent deposit 1001 is operable in conjunction with an EM source positioned nearby, which can efficiently and more directly convey EM energy thereto.

Figure 27:
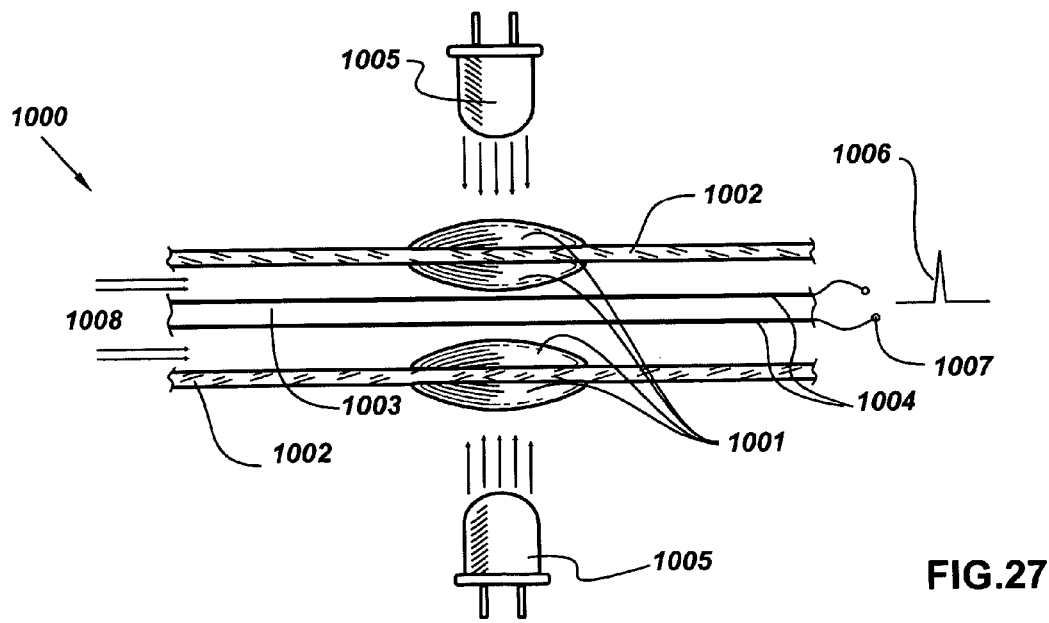
FIG. 27 is a simplified diagram of a detection system incorporating a pyroelectric film, a plurality of electromagnetic spectrum sources, and a plurality of reagents, according to the invention.

In the alternative arrangement illustrated in FIG. 27, the system 1000 provides for two additional reagent deposits 1001. Specifically, a reagent deposit is provided on a top surface of the substrates 1002 and on the bottom surfaces of bottom substrates 1002. In this way, reactions with the target analyte may occur at four different locations.

Figure 28:
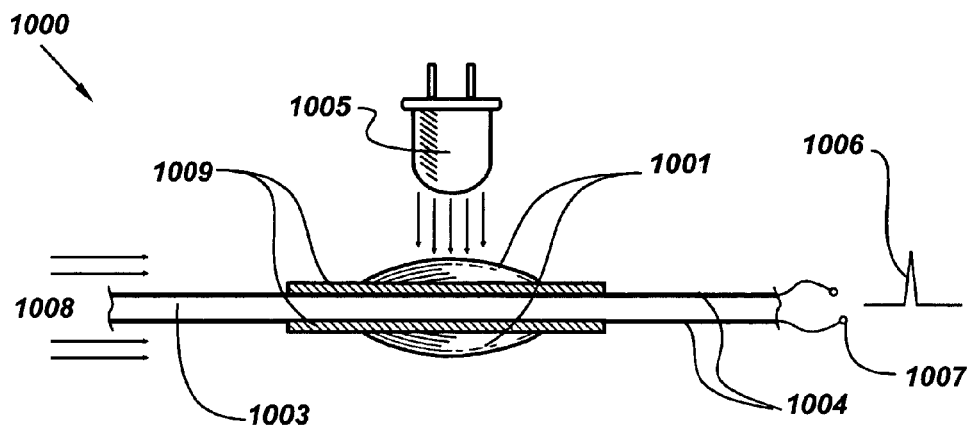
FIG. 28 is a simplified diagram of a detection system incorporating a pyroelectric film, an electromagnetic spectrum emitting source, and a plurality of reagents, according to the invention.

In the alternative arrangement of FIG. 28, the system 1000 employs one pyroelectric film 1003 having metallic conductive surface 1009 on a top surface and on a bottom surface thereof. Further, each of the metallic conductive surfaces 1009 has deposited thereon a reagent deposit 1001.

Figure 29:
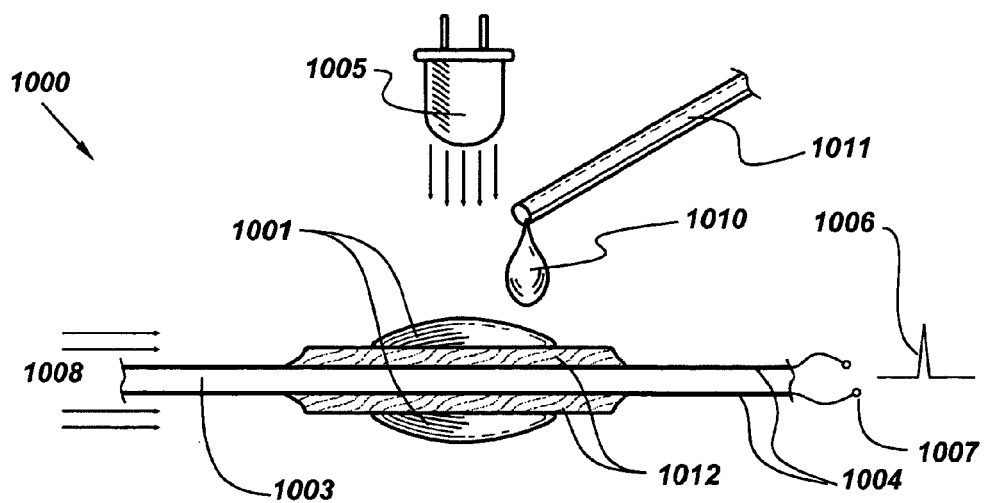
FIG. 29 is a simplified diagram of an alternative embodiment of a detection system incorporating a pyroelectric film, an electromagnetic spectrum emitting source, and a plurality of reagents, and including a developer and developing insert according to the invention.

In the alternative arrangement of FIG. 29, the metallic conductive surface 1009, is replaced with thermal conductive paste 1012 applied on a top and a bottom surface of the pyroelectric film 1003. As previously described with one or more of the alternative embodiments, the arrangement includes a reagent and/or a plurality of reagents and/or developer to be added prior to the sampling after additional reagent and/or developer insert 1010. The additional reagent and/or developer 1010, may be applied by way of a conduit 1011 in the form of a pipette, dropper, and or other applicator.

Figure 30:
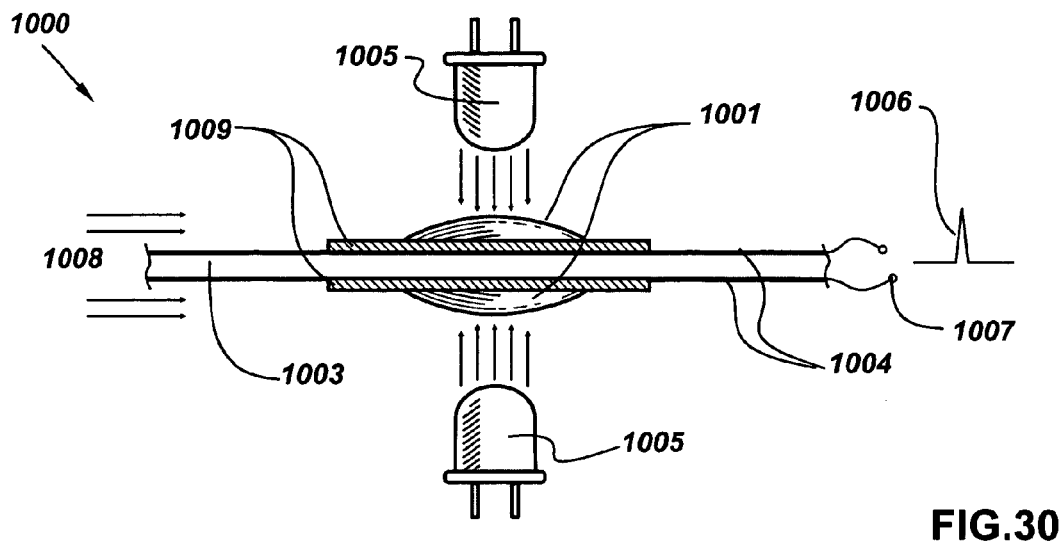
FIG. 30 is a simplified diagram of an alternative embodiment of a detection system incorporating a pyroelectric film, a plurality electromagnetic spectrum emitting sources, and a plurality of reagents, according to the invention.
Figure 31:
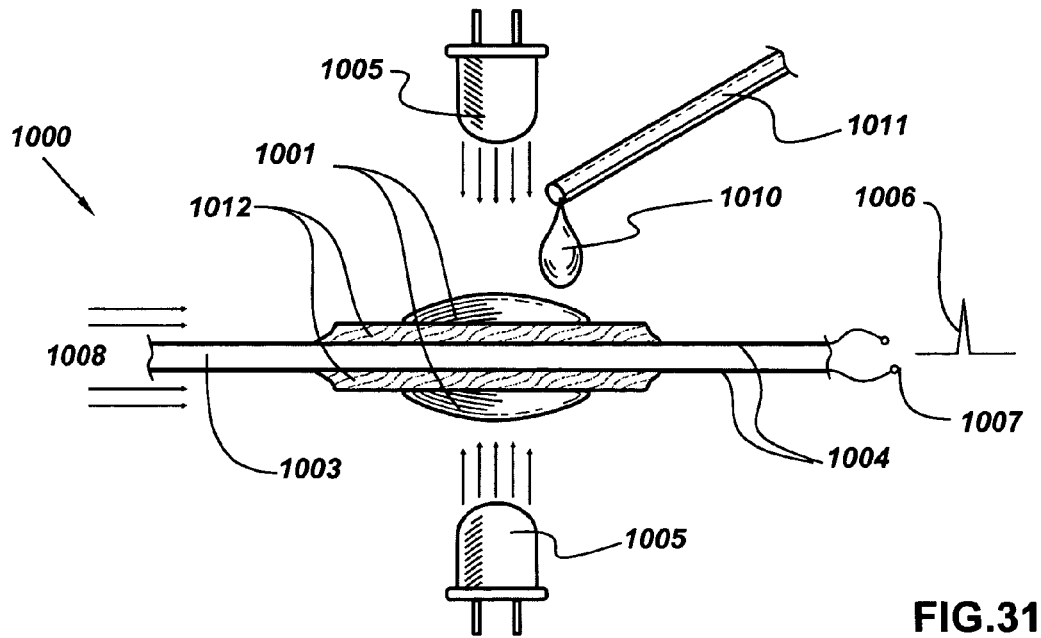
FIG. 31 is a simplified diagram of an alternative embodiment of a detection system incorporating a pyroelectric film, a plurality electromagnetic spectrum emitting sources, and a plurality of reagents, along with a developer and a developer insert according to the invention.

Each of FIG. 30 and FIG. 31 is provided to illustrate yet a further variation of the above described embodiments. In FIG. 30, a second EM source 1005 is used in conjunction with the two reagent deposits 1001 and two metallic conductive surfaces 1009. In the arrangement of FIG. 31, the system 1000 employs a thermally conductive paste 1012 applied on a top and a bottom surface of the pyroelectric film 1003. Further, a second EM source 1005 is positioned above the top reagent deposit 1001 in both FIG. 30 and FIG. 31.

Figure 32:
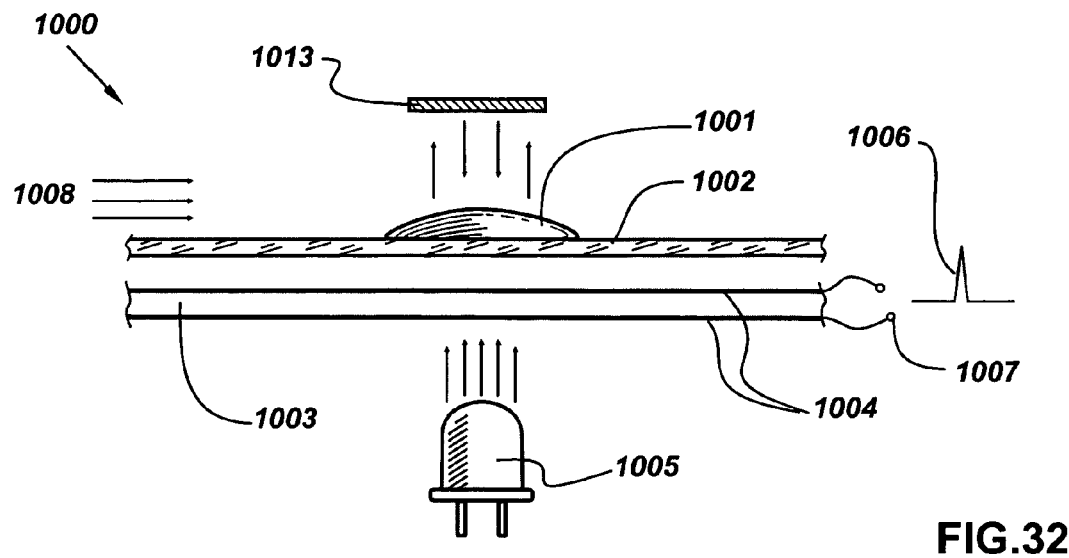
FIG. 32 is a simplified diagram of a detection system incorporating a pyroelectric film, an electromagnetic spectrum emitting source, and a reflective surface, according to the invention.

Now turning to FIGS. 32-36, the system 1000 according to the present invention employs a reflective mirror 1013 to more efficiently convey EM energy from an EM source 1005 to one or more reagent deposits 1001. In FIG. 32, the inventive system 1000 includes a transparent substrate 1002 having a reagent deposit 1001 supported on a top surface. The system 1000 further includes a pyroelectric film 1003 positioned below and spaced apart from the transparent substrate 1002. Moreover, an EM source 1005 is positioned below the pyroelectric film 1003, and is operable to direct energy through the pyroelectric film 1003 and the transparent substrate 1002 to reach the reagent deposit 1001. In a preferred embodiment, a reflective surface 1013 comprises a reflective mirror which is readily commercially available. The reflective mirror 1013 is positioned directly above and spaced apart from the reagent deposit 1001. In this arrangement, the sample fluid flow 1008 is directed above the transparent substrate 1002 and in between the reagent deposit 1001 and the reflective mirror 1013. The reflective mirror 1013 is adapted and positioned so as to reflect EM energy emanating from the reagent deposit 1001, and directing this reflected EM energy back onto the reagent deposit 1001. In this way, the efficiency of the system is increased as well as the sensitivity of the system 1000 without the need for a second EM source.

Figure 33:
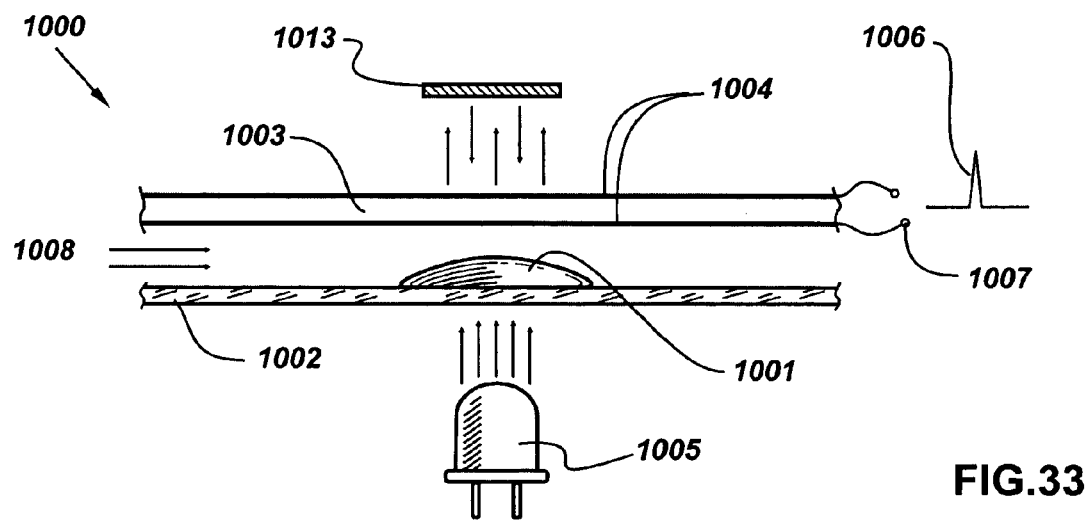
FIG. 33 is a simplified diagram of an alternative embodiment of a detection system incorporating a pyroelectric film, an electromagnetic spectrum emitting source, and a reflective surface, according to the invention.

In the alternative arrangement illustrated in FIG. 33, the pyroelectric film 1003 is positioned above and spaced apart from the transparent substrate 1002, which supports the reagent deposit 1001. Further, the EM source 1005 is positioned below the transparent substrate 1002, and in general vertical alignment with the reagent deposit 1001. In this particular arrangement, the reflective mirror 1013 is positioned above the pyroelectric film 1003 and in general vertical alignment with the reagent deposit 1001 and EM source 1005. At this position, the reflective mirror 1013 can reflect and return EM energy emanating from the reagent deposit 1001. Again, in this way, the efficiency of the system is improved as well as the sensitivity of the inventive system.

Figure 34:
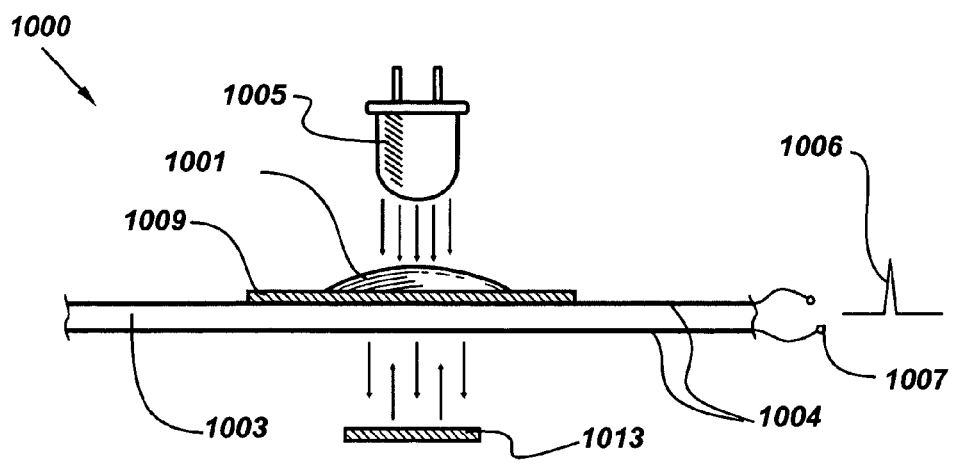
FIG. 34 is a simplified diagram of an alternative embodiment of a detection system incorporating a pyroelectric film, an electromagnetic spectrum emitting source, and a reflective surface, according to the invention.
Figure 35:
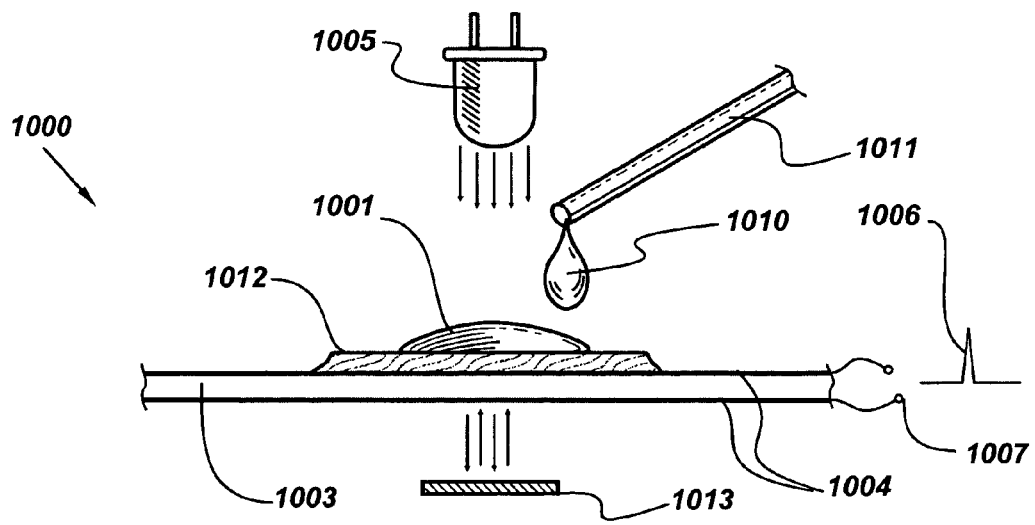
FIG. 35 is a simplified diagram of an alternative embodiment of a detection system incorporating a pyroelectric film, an electromagnetic spectrum emitting source, and a reflective surface along with a developer and a developer insert according to the invention.

In the alternative arrangement illustrated in FIG. 34, the system 1000 employs, in lieu of the transparent substrate 1002, a metallic conductive surface 1009 as described in previous embodiments. Moreover, the EM source 1005 is now located directly above and spaced apart from the reagent deposit 1001. Furthermore, the reflective mirror 1013 is positioned below the pyroelectric film 1003 and in general vertical alignment with both the reagent deposit 1001 and the EM source 1005. In this arrangement, the mirror 1013 is positioned to reflect EM energy directed from EM source 1005 and traveling through the reagent deposit 1001, the metallic conductive surface 1009, and the pyroelectric film 1003. In this way, the intensity of the EM energy irradiated upon the reagent 1001 is intensified, thereby increasing the sensitivity of the inventive system 1001. FIG. 35 is a variation of the arrangement and the system 1000 illustrated in FIG. 34. In lieu of the metallic conductive surface 1009, thermally conductive paste 1012 is employed in a manner similar to one or more of previously described embodiments.

Figure 36:
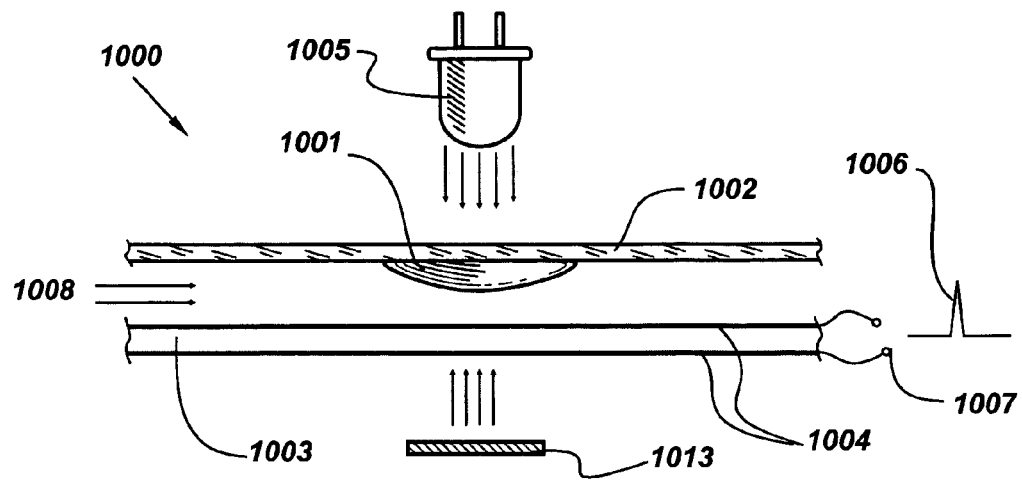
FIG. 36 is a simplified diagram of an alternative embodiment of a detection system incorporating a pyroelectric film, an electromagnetic spectrum emitting source, and a reflective surface, according to the invention.

In the arrangement illustrated in FIG. 36, the system 1000 employs a transparent substrate 1002 having a reagent deposit 1001 supported on a bottom surface. In this alternative arrangement, a reflective mirror 1013 is positioned below the pyroelectric film 1003, which is positioned below and spaced apart from the reagent deposit 1001 and transparent substrate 1002. As illustrated in the figure, the reflective mirror reflects EM energy back through the pyroelectric film 1003 and upon the reagent deposit 1001.

Figure 37:
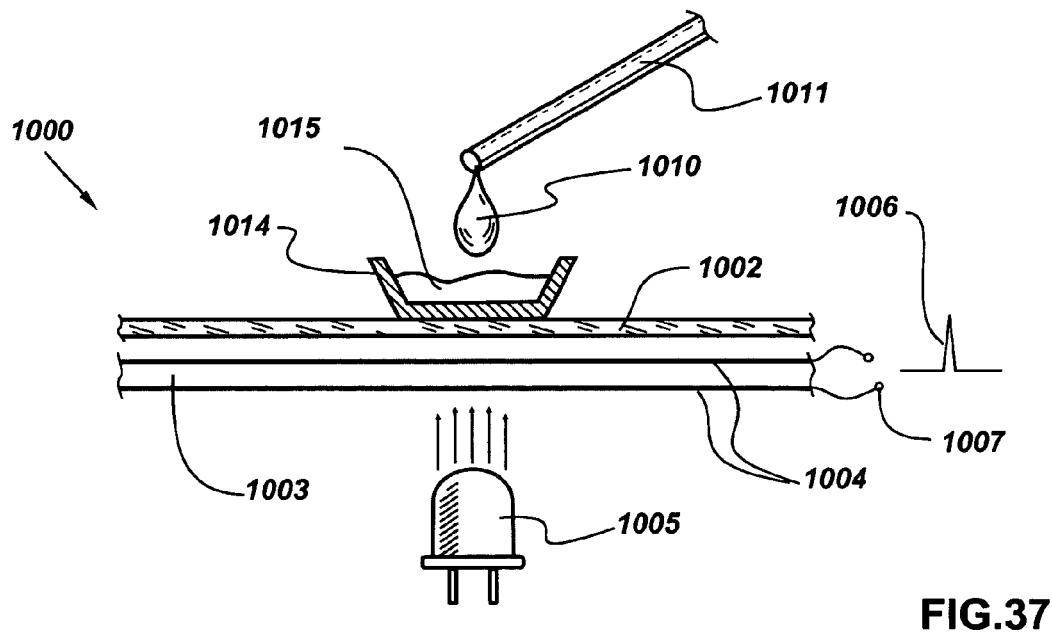
FIG. 37 is yet another alternative embodiment of a detection system according to the invention, incorporating a pyroelectric film, an electromagnetic spectrum emitting source, a container, a developer and a developer insert.

Now turning to FIG. 37, an alternative arrangement for the inventive system 1000 is shown having a transparent substrate 1002 positioned above and spaced apart from the pyroelectric film 1003. In this particular arrangement, the system 1000 further employs a cup or container 1014 positioned on a top surface of the transparent substrate 1002. A sample 1015 is provided in container 1014 for testing purposes to determine whether a target analyte is present in the sample. The cup or container 1014 may be made of a suitable material, such as glass, polypropylene, polyethylene or polyester. A reagent(s) and/or developer 1010 may also be added prior to and after sampling via conduit means 1011. Moreover, in this particular embodiment, the EM source 1005 is positioned below the pyroelectric film 1003 and the transparent substrate 1002, but in general vertical alignment with the target analyte.

Figure 38:
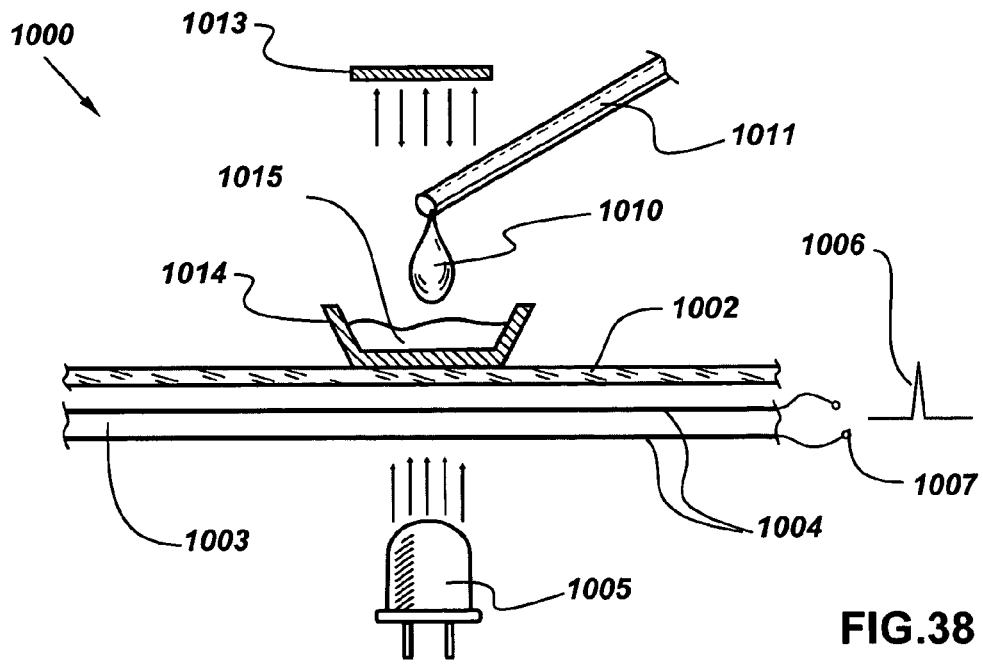
FIG. 38 is yet another alternative embodiment of a detection system according to the invention, incorporating a pyroelectric film, an electromagnetic spectrum emitting source, a container, a developer and a developer insert and a reflective surface.

The alternative arrangement illustrated in FIG. 38 provides for a system 1000 employing a reflective mirror 1013. The reflective mirror 1013 is positioned above the cup or container 1014. In this way, the reflective mirror 1013 can reflect and redirect EM energy originally conveyed from the EM source 1005 positioned below the pyroelectric film 1003. Such use of the reflective mirror 1013 intensifies the EM energy irradiated upon the sample 1015, thereby increasing the sensitivity of the inventive system 1000.

Figure 39:
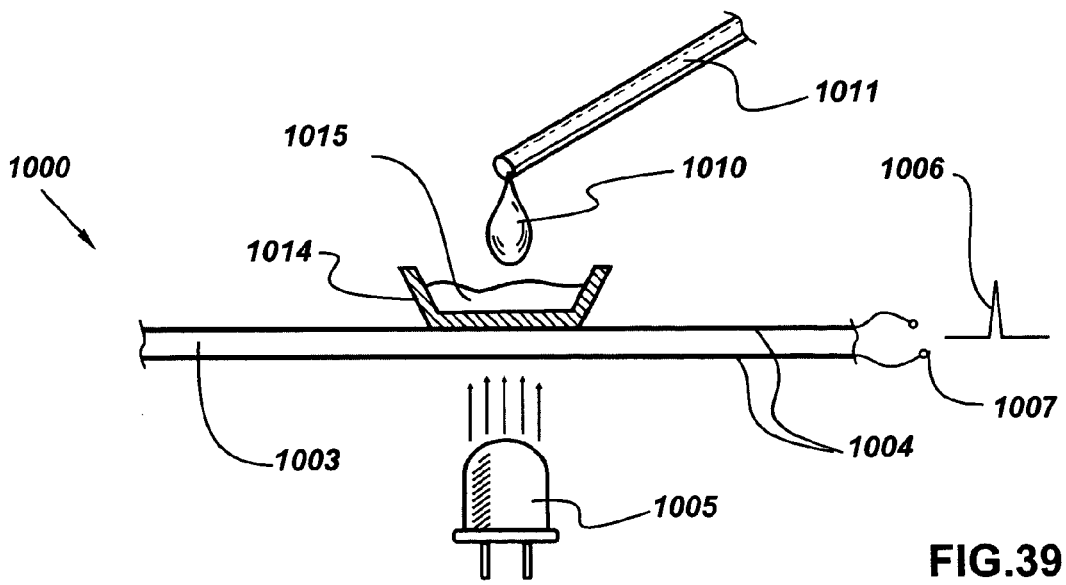
FIG. 39 is yet another alternative embodiment of a detection system according to the invention, incorporating a pyroelectric film, an electromagnetic spectrum emitting source, a container, a developer and a developer insert.

In the alterative arrangement illustrated in FIG. 39, the system 1000 employs a cup or container 1014 for retaining or holding the sample 1015. The conductive cup or container 1014 is positioned directly on the pyroelectric film 1003 and in general vertical alignment with the EM source 1005.

Figure 40:
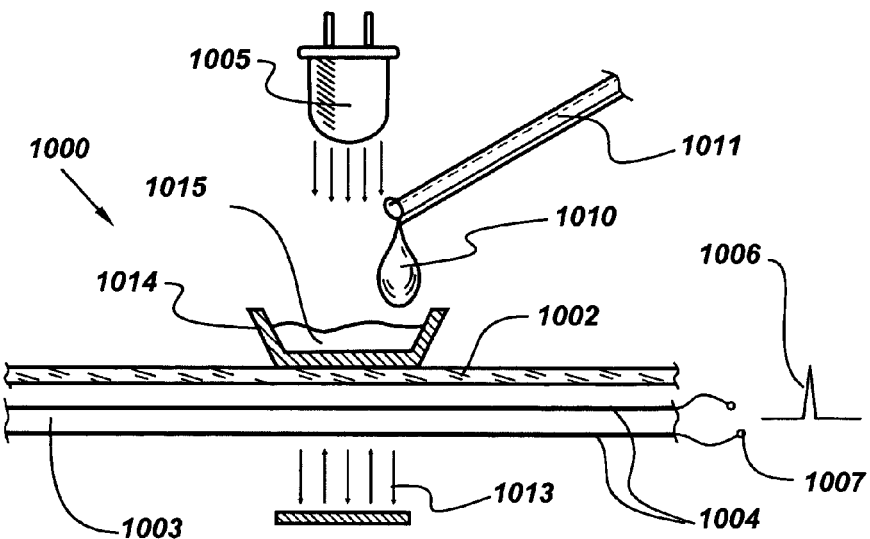
FIG. 40 is yet another alternative embodiment of a detection system according to the invention, incorporating a pyroelectric film, an electromagnetic spectrum emitting source, a reflective surface, a container, a developer and a developer insert.

In the alternative arrangement illustrated in FIG. 40, the inventive system 1000 employs both a transparent substrate 1002 and a pyroelectric film 1003. The transparent substrate 1002 supports a cup or a container 1014 having the sample thereon 1015, and in position to receive an additional reagent and/or developer 1010, via a conduit means 1011. Moreover, the pyroelectric film 1003 is positioned below and spaced apart from the transparent substrate 1002 and a reflective mirror 1013 is positioned below and spaced apart from the bottom surface of the pyroelectric film 1003. As shown in the Figure, the EM source 1005 is positioned above the cup or container 1014 and in general vertical alignment with the cup or container 1014, the analyte 1015, and the reflective mirror 1013. The use of the reflective mirror 1013, in this way, intensifies the EM energy directed upon the analyte 1015, thereby increasing the sensitivity of the inventive system 1000.

Figure 41:
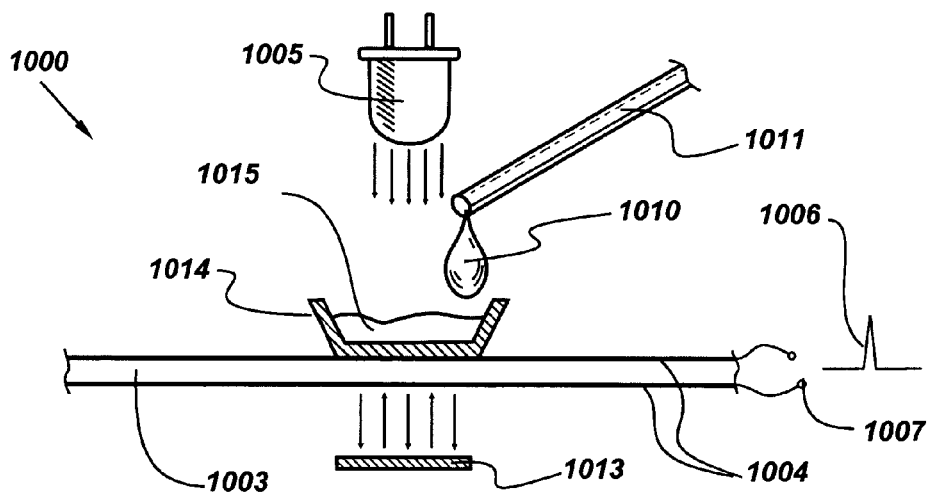
FIG. 41 is yet another alternative embodiment of a detection system according to the invention, incorporating a pyroelectric film, an electromagnetic spectrum emitting source, a reflective surface, a developer and a developer insert.

In the arrangement illustrated in FIG. 41, the system 1000 provides a cup or container 1014 having the sample 1015 therein, directly on a top surface of the pyroelectric film 1003. Moreover, the reflective mirror 1013 is positioned below and spaced apart from the pyroelectric film 1003, while the EM source 1005 is positioned above and spaced apart from the cup or container 1014. Each of the EM sources 1005, the sample 1015 retained in the cup or container 1014, and the reflective mirror 1013 are in general vertical alignment, so as to intensify the EM energy irradiated upon the reagent 1015 (in a manner similar to those described in previous embodiments).

Figure 42:
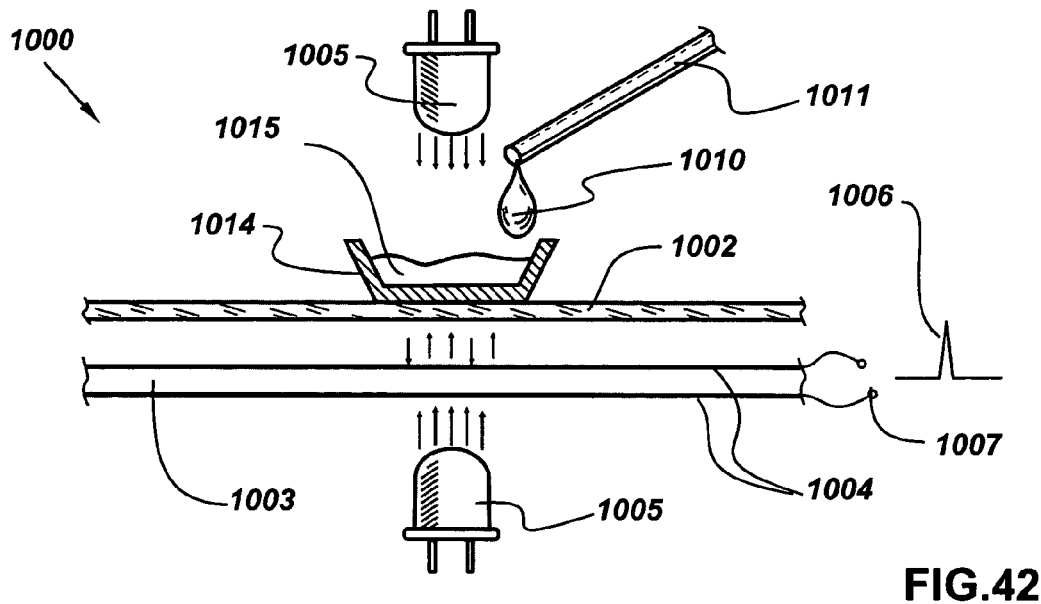
FIG. 42 is yet another alternative embodiment of a detection system according to the invention, incorporating a pyroelectric film, a plurality electromagnetic spectrum emitting sources, a container, a developer and a developer insert.

In the arrangement illustrated in FIG. 42, the inventive system 1000 employs both a transparent substrate 1002 and a pyroelectric film 1003. EM sources 1005 are positioned both below the pyroelectric film 1003 and above the transparent substrate 1002, and in general vertical alignment with the cup or container 1014. The EM source 1005 can, therefore, direct EM energy through the sample 1015 from two directions.

Figure 43:
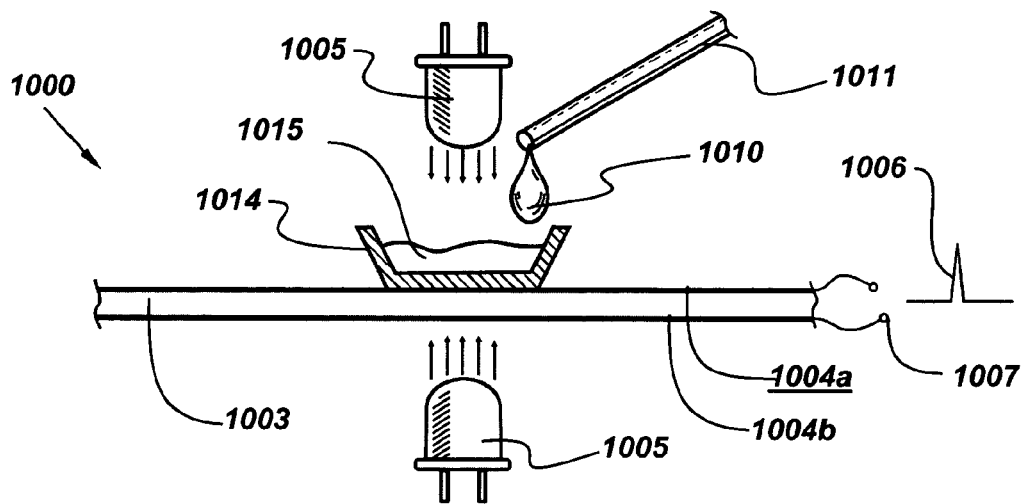
FIG. 43 is yet another alternative embodiment of a detection system according to the invention, incorporating a pyroelectric film, a plurality electromagnetic spectrum emitting sources, a container, a developer and a developer insert.

FIG. 43 illustrates yet another alternative arrangement for the inventive system 1000. The system 1000 includes a conductive cup or container 1014 positioned directly on a conductive top metallic surface 1004a of the pyroelectric film 1003. EM sources 1005 are positioned above and below the pyroelectric film 1003 to direct EM energy through the reagent 1015 provided in the cup or container 1014.

In another arrangement, the inventive system employs a transparent substrate to support a plurality of reagent deposits, at least one of which is on a top surface and the other on a bottom surface. The system further employs a pyroelectric film, as previously described, positioned below and spaced apart from the transparent substrate and the reagent deposit supported thereon. The illustrated system specifically utilizes the use of fiber optic cables to convey EM energy, i.e., light from one or more EM sources. In the illustrated arrangement, the fiber optic cable includes four separate fiber optic cables. One cable directs light from the EM source to the top reagent deposit. A second cable directs light to a top surface of the transparent substrate directly above but on opposite sides of the bottom reagent deposit. The system further provides two additional fiber optic cables to direct light towards the bottom metallic conductive surface of pyroelectric film. Each of the bottom fiber optic cables is positioned in general vertical alignment with one of the reagent deposits, so as to direct light through the pyroelectric film and in the direction of each of the reagent deposits.

In each of the previously described alternative arrangements of the inventive system 1000, a variety of additional components and accessories may be employed to improve the performance of the system 1000 or to better suit certain applications. For example, in various applications, a prefilter may be provided on the exterior or interior of a badge containing or embodying the system 1000. In the further embodiments, the prefiltering may be provided over a membrane or layer that covers a reagent and/or may be impregnated within the reagent itself. In yet further embodiments, filters may be provided to prevent interferent(s) from contacting the reagent on the film (which would otherwise contaminate the reagent). Filters may also be provided to prevent moisture from contacting the reagent or the pyroelectric film. Additional filters may be provided as well, to absorb the interferent, contaminant, or moisture.

Other components or means may be employed to improve the integrity and thus the performance of the detection system. For example, exit ports may be provided to vent the ambient environment. Such an exit port may be shielded to prevent moisture and/or water from entering the system. Further, when a pump is used, a replaceable charcoal filter may be provided at the exit side of the badge and before the sample is drawn through the pump. The pump is preferably a modular, plug-in design that can be removed from a basic detection system unit, disposed of, and then retained for use with another unit. In certain embodiments, the badge and the pump are one integrated unit or may be separate. When the badge and the pump are separate, the pump may be housed in a flexible clear plastic or flexible pouch of some other material that is impervious to chemical agents (e.g., for six hours to help ensure easy decontamination). The badge and/or pump may be powered by a variety of ways: batteries, re-chargeable batteries, AC power supply, DC power supply, a hand crank or pump and spring mechanism; solar energy; and/or wind energy.

If the pump and badge are housed together or separately, a variety of information may be stored in the pump or badge. These include (algorithm) software, measurement readings; display; the alarms, computer interface; memory; measurement ranges; etc.

In another aspect of certain embodiments of the system 1000, the pyroelectric film 1003 may be connected to a filter that removes specific interferents such as anilines and amines from TDI reagent. The pyroelectric film 1003 may be used with a variety of color codes to detect various detected agents, e.g., nerve agents, blister agents, choking agents, and blood agents. For example, nerve agent detectors may be provided in red stripes and blister agent detectors may be provided in yellow stripes and a dot. Likewise, different detectors may be labeled with military or international markings for detecting various detectors.

Another component that may be advantageously integrated with the system 1000 previously described, is a microprocessor or plurality of microprocessors having programmed therewith a suitable algorithm and software. The algorithm and software may be adapted for performing and/or controlling various functions, and may be remotely monitored, downloaded, upgraded, and processed via electronic mail and/or telephone.

With the aid of the microprocessor, the EM source or sources may irradiate at the same time, continuously, at intervals, or sequentially, during sampling and/or after sampling. Moreover, the EM source may interrogate the output of the pyroelectric film 1003 and reagent 1001 at any time from the beginning to the end of the sampling and, for any portion of time within the sampling period. The microprocessor may be also used to set the frequency of the interrogation based upon, for example, time and the rate of increase or decrease in the absolute change in the output, and from the increase or decrease in the average output of previous readings compared to the most recent reading. Additionally, the frequency of interrogation may be based upon the percentage of the full-scale range, the threshold limit value (TLV), the time weigh average (TWA), the short term exposure limit (STEL) and/or the permissible exposure limit (PEL). Such frequency may also be based upon the percentage of the alarm set point, or as an absolute unit of measure from the alarm set point. With the aid of the microprocessor, the system may be able to correct itself for zero drift and calibration drift, and for degradation of the reagent 1001 and/or the pyroelectric film 1003 over time, temperature range, or over humidity range. Adding to may perform this or deducting from the output of previous readings, the difference between the last reading and a factor established in lookup tables (based upon temperature, humidity, expired shelf life, exposed pressure, target analyte concentration, and any combination thereof). An alternative algorithm may be employed that adds to or deducts from the output of the last reading, the difference between the last reading and the prior reading or an average of prior readings. Furthermore, the microprocessor may be used to calculate the amount or rate of change for a comparison with an alarm set point. This may be done by comparing the current readings, in units such as ppb, ppm, percent volume, and/or percent of change in readings taken since the last sample and then a comparison made to an alarm set point established as a specific number increases or decreases. This specific number may be based in the unit volume and/or specified as specific percentage increase or decrease in the unit volume and/or a specified minimum/maximum percentage increase of or decrease.

With the aid of the microprocessor, the inventive detection system may be operable to trigger an alarm based upon the rate of change that exceeds a set point. The alarm may include audio, visual, and vibrating alarms. Furthermore, the microprocessor may be used to record the time and/or date of signal output in the alarm, as well as the concentration of the target analyte. The system may also be able to store all alarms (high or low), the duration of the alarm, and the concentration of the detected analyte.

The microprocessor also makes it possible, in a variety of ways, to measure more than one range or a target analyte independently of different reagents, and at different ranges. Furthermore, measurements may be made for more than one target analyte and for more than one range for each of the target analytes. In another variation of the inventive system, the microprocessor may be used to provide different flow rates and/or face velocity at each reagent and/or each range of the target analyte. These functions may be formed simultaneously and/or sequentially. Also, different flow rates and velocities may be provided for each reagent, and at different pressures.

Other improvements to the system may be included. For example, the reagent deposit may shift and/or increase the intensity of the reflected EM spectrum upon biological interaction with the analyte. Alternatively, the reagent deposit may shift and or increase the intensity of the reflected EM spectrum upon physical interaction with the analyte. The system may include an immunoassay sensor and method for detecting the presence of a particular analyte comprising a solid substrate which changes pyroelectric properties. An antibody to which the analyte binds immobilized on the solid substrate may be included. A transducer surface may provide at least one electrophoretic separation layer. An electrode means provides a voltage signal indicative of heat generated on said transducer surface. A means of irradiation of the transducer surface with light frequency whereby heat is generated is included. A tagged form of the analyte displaceably binds to the antibody. It has a lower binding energy than an untagged analyte. The untagged analyte displaces the tagged analyte and binds to the antibody when the antibody with tagged analyte contacts a sample containing the untagged analyte. The antibody with bound tagged analyte has a pyroelectric property which is changed by displacement of the tagged analyte by untagged analyte. The antibody with bound tagged analyte forms a solid state system.

The sensor may further comprise a pyroelectric detector operatively associated with the solid substrate to detect changes in the pyroelectric property produced by displacement of the tagged analyte by untagged analyte. The solid substrate of the sensor may comprise a membrane. The sensor transducer surface is transparent at a pre-selected light frequency so as to irradiate the antibody to which the analyte binds immobilized on the solid substrate. The antibody may be a monoclonal antibody, a pool of monoclonal antibodies, or a polyclonal antibody. The system may further comprise an immunoassay sensor and method based on immunochromatograpy techniques for detecting the presence of a particular analyte and comprise a sample delivery pad function to filter out any undesired matter and to hold analyte so that it can slowly wick to an antibody conjugate release pad. A conjugate antibody release pad that contains pre-selected conjugated antibody to bind to analyte and migrate to analysis pad. An analysis pad holds the conjugated antibody bound analyte. A transducer surface proves at least one electrophoretic separation layer adjacent to the analysis pad. An electrode means provides a voltage signal indicative of heat generated on the transducer surface. A means of irradiation of the transducer surface with light frequency is provided to generate heat. A buffer controls a pH balance of the sample, such as PBS. A surfactant prevents formation of aggregates, such as Triton-x-100. A means of separating the conjugate antibody release pad from the analysis pad after conjugated antibody bound flow to the analysis pad prevents the sample from flowing back to the conjugate antibody release pad. The sensor may further comprise a pyroelectric detector operatively associated with the analysis pad to detect changes in a pyroelectric property produced by displacement of the tagged analyte by untagged analyte. The transducer surface is transparent at a certain light frequency so as to irradiate the conjugated antibody to which the analyte binds. The antibody may be a monoclonal antibody, a pool of monoclonal antibodies, or a polyclonal antibody.

Although the present system, apparatus and method of detecting a target analyte and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. For example, various exemplary configurations of a detection system have been described. As one of ordinary skill in the art will readily appreciate from the disclosure of the present invention, various elements from measurement or instrumentation technology, or measuring methods or steps, presently existing or later to be developed that perform substantially the same function or achieve substantially the same result as the corresponding embodiments described herein may be utilized according to the present invention. Accordingly, the appended claims are intended to include within their scope such machines, apparatus, methods, or steps.

What is claimed is:

1. In a system for measuring a concentration of at least one target analyte, a sensor carrier subsystem comprising:
    a transparent substrate having a first surface, a second surface disposed opposite of said first surface, and a reagent deposit supported on said first surface, said reagent deposit being reactive to an exposure to the target analyte and further characterized by a capacity to absorb electromagnetic energy, wherein said absorption capacity changes after said reagent deposit reacts upon the exposure to the target analyte such that said change in capacity is indicative of an amount of the exposure to the target analyte;
    an electromagnetic spectrum emitting source (EM source) positioned proximal to said transparent substrate, said EM source being operable to irradiate said reagent deposit by way of a path directed through said transparent substrate; and
    a pyroelectric transducer positioned adjacent to said reagent deposit to detect energy absorbed by said reagent deposit upon irradiation by said EM source and generate output signals indicative of the detected energy, such that said output signal is indicative of the exposure to the target analyte; and
    wherein the reagent deposit is spaced apart from the pyroelectric transducer.

2. The sensor carrier subsystem of claim 1, wherein said pyroelectric transducer is positioned intermediate said transparent substrate and said EM source, such that said EM source is operable to irradiate said reagent deposit by way of the path being directed through said pyroelectric transducer.

3. The sensor carrier subsystem of claim 1, wherein said transparent substrate is positioned intermediate said transducer and said EM source.

4. The sensor carrier subsystem of claim 1, further comprising a second EM source positioned proximal said reagent deposit such that said first surface is positioned intermediate said second surface and said second EM source.

5. The sensor carrier subsystem of claim 4, wherein said pyroelectric transducer is positioned intermediate said transparent substrate and said second EM source, such that said second EM source is operable to irradiate said reagent deposit by way of the path being directed through said pyroelectric transducer.

6. The sensor carrier subsystem of claim 5, wherein said pyroelectric transducer is a transparent pyroelectric film.

7. The sensor carrier subsystem of claim 1, wherein said reagent deposit is supported on said transparent substrate such that said reagent deposit faces and is spaced apart from said pyroelectric transducer; and
    wherein said transparent substrate and said pyroelectric transducer are spaced apart so as to provide a sample environment flow path therebetween.

8. The sensor carrier subsystem of claim 1, wherein said transparent substrate further includes a second reagent deposit supported on one of said first and second surfaces.

9. The sensor carrier subsystem of claim 8, wherein said second reagent deposit is disposed on said second surface in substantially vertical alignment with said first reagent deposit supported on said first surface.

10. The sensor carrier subsystem of claim 8, further comprising a second EM source positioned relative to said first EM source, such that said transparent substrate, said first and second reagent deposits, and said pyroelectric transducer are positioned intermediate said first and second EM sources.

11. The sensor carrier subsystem of claim 8, further comprising a second EM source positioned proximal said first EM source, such that said pyroelectric transducer is positioned intermediate said transparent substrate and said first and second EM sources.

12. The sensor carrier subsystem of claim 1, further comprising a second substrate supporting a reagent deposit on a first surface of said second substrate and spaced apart from said pyroelectric transducer such that said second reagent deposit faces said pyroelectric transducer, wherein said EM source is operable to irradiate said second reagent deposit by way of a path directed through said transparent substrate and through said pyroelectric transducer.

13. The sensor carrier subsystem of claim 1, further comprising:
    a second transparent substrate having a first surface and a second surface disposed opposite of said first surface, wherein a second reagent deposit is supported on said first surface and spaced apart from said pyroelectric transducer such that said second reagent deposit faces said pyroelectric transducer; and
    a second EM source positioned proximal said second surface of said second transparent substrate and operable to irradiate said second reagent deposit by way of a path directed through said first and second surfaces of said second transparent substrate.

14. The sensor carrier subsystem of claim 1, further comprising a reflective surface positioned to redirect energy emitted by said EM source through said reagent deposit, said reflective surface being positioned relative to said EM source such that said transparent substrate, said reagent deposit, and said pyroelectric transducer are positioned intermediate said reflective surface and said EM source.

15. The sensor carrier subsystem of claim 14, wherein said reflective surface is a mirror spaced directly across from said reagent deposit.

16. The sensor carrier subsystem of claim 1, wherein said pyroelectric transducer includes a pyroelectric film having conductive electrodes thereon for transmitting an output signal.

17. The sensor carrier subsystem of claim 16, wherein said pyroelectric film is substantially transparent to said energy irradiated from said EM source.

18. The sensor carrier subsystem of claim 17, wherein said EM source is selected from a group consisting of visible light emitting sources, UV light sources, IR light emitting sources and microwave sources.

19. The sensor carrier subsystem of claim 1 wherein said reagent deposit is affecting a reflected EM spectrum upon chemical interaction with the analyte by one or two means consisting from shifting the reflected EM spectrum and changing the intensity of the reflected EM spectrum.

20. The sensor carrier subsystem of claim 19, wherein said EM source is a light emitting source and said pyroelectric transducer is adapted to detect the amount of heat absorbed in said reagent deposit upon illumination by said light emitting source.

21. The sensor carrier subsystem of claim 1, further comprising a fiber optic cable operatively or light bar associated with said EM source to direct EM energy emitted from the EM source via said path to said reagent deposit.

22. The sensor carrier subsystem of claim 1, wherein said reagent deposit is affecting a reflected EM spectrum upon biological interaction with the analyte by one or two means consisting from shifting the reflected EM spectrum and changing the intensity of the reflected EM spectrum.

23. The sensor carrier subsystem of claim 1, wherein said reagent deposit is affecting a reflected EM spectrum upon physical interaction with the analyte by one or two means consisting from shifting the reflected EM spectrum and changing the intensity of the reflected EM spectrum.

24. The sensor carrier subsystem of claim 1, further comprising an immunoassay sensor for detecting a presence of a particular analyte comprising:
a solid substrate, which changes pyroelectric properties;
an antibody, to which the analyte binds, immobilized on the solid substrate;
a transducer surface providing at least one electrophoretic separation layer;
an electrode means that provides a voltage signal indicative of heat generated on said transducer surface;
a means of irradiation of the transducer surface by the EM source whereby heat is generated; and,
a tagged form of the analyte displaceably bound to the antibody and having lower binding energy to the antibody than untagged analyte, wherein untagged analyte will displace tagged analyte and bind to the antibody when the antibody with tagged analyte contacts a sample containing untagged analyte, the antibody with bound tagged analyte having pyroelectric property, which is changed by displacement of tagged analyte by untagged analyte, the antibody with bound tagged analyte forming a solid state system.

25. The immunoassay sensor of claim 24, further comprising a pyroelectric detector operatively associated with the solid substrate to detect changes in pyroelectric property produced by displacement of the tagged analyte by untagged analyte.

26. The immunoassay sensor of claim 24, wherein the solid substrate is a membrane.

27. The immunoassay sensor of claim 24, wherein the transducer surface is transparent at a light frequency so as to irradiate said antibody, to which the analyte binds, immobilized on the solid substrate.

28. The immunoassay sensor of claim 24, wherein the antibody is one or more selected from a group consisting of a monoclonal antibody, a pool of monoclonal antibodies, and a polyclonal antibody.

29. The sensor carrier subsystem of claim 1 further comprising an immunoassay sensor based on immunochromatograpy techniques for detecting the presence of a particular analyte comprising:
a conjugate antibody release pad that contains at least one pre-selected conjugated antibody to bind to the target analyte to create a conjugated antibody bound analyte;
a sample delivery pad to filter out any undesired matter and to hold the conjugated antibody bound analyte so that said conjugated antibody bound analyte can slowly wick to the antibody conjugate release pad;
an analysis pad to hold the conjugated antibody bound analyte;
a transducer surface providing at least one electrophoretic separation layer adjacent to the analysis pad;
an electrode means that provides a voltage signal indicative of heat generated on said transducer surface;
a means of irradiation of the transducer surface with light frequency whereby heat is generated;
a buffer to control a pH level of the sample;
a surfactant to prevent formation of an aggregate; and,
a means of separating said conjugate antibody release pad from said analysis pad after a bound conjugated antibody flows to the analysis pad to prevent the sample from flowing back to the conjugate antibody release pad.

30. The sensor carrier subassembly of claim 29, further comprising a pyroelectric detector operatively associated with the analysis pad to detect changes in pyroelectric property produced by displacement of a tagged analyte by an untagged analyte.

31. The immunoassay sensor of claim 29, wherein the transducer surface is transparent at said light frequency so as to irradiate said conjugated antibody to which the target analyte binds.

32. The immunoassay sensor of claim 29, wherein the at least one pre-selected conjugated antibody is one or more selected from a group consisting of a monoclonal antibody, a pool of monoclonal antibodies, and a polyclonal antibody.

33. The systems of claim 1, wherein the EM source generates energy in a microwave frequency spectrum.

34. The systems of claim 1, wherein the reader contains a timer.

35. The systems of claim 1, wherein the reagent is reversible and reusable.

36. The systems of claim 1, wherein the reagent is non-reversible and reusable.

37. The systems of claim 1, wherein the reagent is an inkjet printing.

38. The systems of claim 1, wherein the reagent is a screen.

39. The systems of claim 1, wherein the reagent is cast in a mold onto the substrate such that the molded reagent is symmetrical on the top, bottom and sides.

40. The systems of claim 1, wherein the EM source is located on a removable assembly subcomponent of the system.

41. The systems of claim 1, wherein a filter assembly is located on a removable assembly subcomponent of the system.

42. The systems of claim 1, wherein said transparent substrate contains a memory chip.

43. A system for detecting a presence of at least one target analyte in a sample local environment, said system comprising:
a transparent substrate having a first surface, a second surface disposed opposite of said first surface, and a reagent deposit supported on said first surface, said reagent deposit being reactive to an exposure to the target analyte and further characterized by a capacity to absorb electromagnetic energy, wherein said absorption capacity changes after said reagent deposit reacts upon the exposure such that said change in capacity is indicative of the exposure to the target analyte;

an electromagnetic spectrum emitting source (EM source) positioned proximal to said transparent substrate and closer to the second surface than to the first surface, said EM source being operable to irradiate said reagent deposit by way of a path directed through said transparent substrate;

a pyroelectric transducer positioned proximal to said reagent deposit to detect energy absorbed by said reagent deposit upon irradiation by said EM source and generate output signals indicative of the detected energy, such that said output signal is indicative of the exposure to the target analyte;

a reader operatively associated with said pyroelectric transducer to receive said output signals, and communicate, therefrom, an indication of the presence of the target analyte in the sample local environment, and wherein the reagent deposit is spaced apart from the pyroelectric transducer.

44. The system of claim 43, wherein said pyroelectric transducer is positioned intermediate said transparent substrate and said EM source, such that said EM source is operable to irradiate said reagent deposit by way of the path being directed through said pyroelectric transducer.

45. The carrier subsystem of claim 43, wherein said transparent substrate is positioned intermediate said transducer and said EM source.

46. The system of claim 43, further comprising a second EM source positioned proximal said reagent deposit such that said first surface is positioned intermediate said second surface and said second EM source.

47. The system of claim 46, wherein said pyroelectric transducer includes a transparent pyroelectric film positioned intermediate said transparent substrate and said second EM source, such that said second EM source is operable to irradiate said reagent deposit by way of a path directed through said pyroelectric transducer.

48. The system of claim 43, wherein said reagent deposit is colorimetrically reactive to a target analyte and said EM source is a light emitting diode.

49. The system of claim 43, wherein said reagent deposit is supported on said transparent substrate such that said reagent deposit faces and is spaced apart from said pyroelectric transducer and wherein said transparent substrate and said pyroelectric transducer are spaced apart so as to provide a sample environment flow path therebetween.

50. The system of claim 43, wherein said transparent substrate further includes a second reagent deposit supported on said second surface and disposed on said second surface in substantially vertical alignment with said first reagent deposit supported on said first surface.

51. The subsystem of claim 43, further comprising a second substrate supporting a reagent deposit on a first surface of said second substrate and spaced apart from said pyroelectric transducer such that said second reagent deposit faces said pyroelectric transducer, wherein said EM source is operable to irradiate said second reagent deposit by way of the path being directed through said pyroelectric transducer.

52. The systems of claim 43, wherein the EM source generates energy in a microwave frequency spectrum.

53. The systems of claim 43, wherein the reader contains a timer.

54. The systems of claim 43, wherein the reagent is reversible and reusable.

55. The systems of claim 43, wherein the reagent is non-reversible and reusable.

56. The systems of claim 43, wherein the reagent is an inkjet.

57. The systems of claim 43, wherein the reagent is a screen printing.

58. The systems of claim 43, wherein the reagent is cast in a mold onto the substrate such that the molded reagent is symmetrical on the top, bottom and sides of the substrate.

59. The systems of claim 43, wherein the EM source is located on a removable assembly subcomponent of the system.

60. The systems of claim 43, wherein the fitter assembly is located on a removable assembly subcomponent of the system.

61. The systems of claim 43, wherein said transparent substrate contains a memory chip.

* * * * *